US011906528B2

(12) United States Patent
Tarca et al.

(10) Patent No.: US 11,906,528 B2
(45) Date of Patent: Feb. 20, 2024

(54) KITS AND METHODS TO DISTINGUISH FALSE LABOR AND TRUE LABOR

(71) Applicants: Wayne State University, Detroit, MI (US); The United States of America, as Represented by the Secretary, Department of Health & Human Service, Bethesda, MD (US)

(72) Inventors: Adi L. Tarca, South Lyon, MI (US); Piya Chaemsaithong, Shatin (HK); Tinnakorn Chaiworapongsa, Grosse Pointe Park, MI (US); Sonia S. Hassan, Novi, MI (US); Roberto Romero, Grosse Pointe, MI (US)

(73) Assignees: Wayne State University, Detroit, MI (US); The United States of America, as Represented by the Secretary, Department of Health & Human Services, Bethesda, MD (US)

( * ) Notice: Subject to any disclaimer, the term of this patent is extended or adjusted under 35 U.S.C. 154(b) by 0 days.

(21) Appl. No.: 17/525,717

(22) Filed: Nov. 12, 2021

(65) Prior Publication Data

US 2022/0065867 A1 Mar. 3, 2022

Related U.S. Application Data

(62) Division of application No. 15/773,980, filed as application No. PCT/US2016/060819 on Nov. 7, 2016, now Pat. No. 11,204,354.

(60) Provisional application No. 62/251,517, filed on Nov. 5, 2015.

(51) Int. Cl.
| | | |
|---|---|---|
| G01N 33/53 | (2006.01) | |
| G01N 33/68 | (2006.01) | |
| G16B 5/00 | (2019.01) | |
| G16B 5/20 | (2019.01) | |
| G01N 33/543 | (2006.01) | |
| G06F 17/18 | (2006.01) | |

(52) U.S. Cl.
CPC ......... *G01N 33/689* (2013.01); *G01N 33/543* (2013.01); *G06F 17/18* (2013.01); *G16B 5/00* (2019.02); *G16B 5/20* (2019.02); *C12Y 101/01205* (2013.01); *C12Y 504/02* (2013.01); *G01N 2333/4727* (2013.01); *G01N 2800/368* (2013.01)

(58) Field of Classification Search
None
See application file for complete search history.

(56) References Cited

U.S. PATENT DOCUMENTS

| | | |
|---|---|---|
| 4,444,879 A | 4/1984 | Foster et al. |
| 5,420,016 A | 5/1995 | Boguslaski et al. |
| 5,516,702 A | 5/1996 | Senyei et al. |
| 2002/0095073 A1 | 7/2002 | Jacobs et al. |
| 2007/0178605 A1 | 8/2007 | Mor et al. |
| 2011/0223622 A1 | 9/2011 | Smith |
| 2014/0045915 A1 | 2/2014 | Skog et al. |
| 2014/0186332 A1 | 7/2014 | Ezrin et al. |
| 2018/0321250 A1 | 11/2018 | Tarca et al. |

FOREIGN PATENT DOCUMENTS

WO  WO2012021944 A1  2/2012

OTHER PUBLICATIONS

Dayarian, et al., "Predicting protein phosphorylation from gene expression: top methods from the Improver Species Translation Challenge," Bioinformatics, vol. 31, No. 4, 2015, pp. 462-470.
Di Quinzio, et al., "Proteomic analysis of human cervico-vaginal fluid displays differential protein expression in association with labor onset at term," Journal of Proteome Research, vol. 7, No. 5, 2008, pp. 1916-1921.
Erez, et al., "High tissue factor activity and low tissue factor pathway inhibitor concentrations in patients with preterm labor," Journal of Maternal-Fetal & Neonatal Medicine, vol. 23, No. 1, 2012, pp. 23-33.
Heng, et al., "Human cervicovaginal fluid biomarkers to predict term and preterm labor," Frontiers in Physiology, vol. 6, No. 151, 2015, 18 pages.
Keren-Politansky, et al., "The coagulation profile of preterm delivery," Thrombosis Research, vol. 133, No. 4, 2014, pp. 585-589.
Mittal, et al., "Characterization of the myometrial transcriptome and biological pathways of spontaneous human labor at term," Journal of Perinatal Medicine, vol. 38, No. 6, 2010, pp. 617-643.
Tarca, et al., "Methodological approach from the Best Overall Team in the sbv Improver Diagnostic Signature Challenge," Systems Biomedicine, vol. 1, No. 4, 2013, pp. 217-227.
Tarca, et al., "Strengths and limitations of microarray-based phenotype prediction: lessons learned from the Improver Diagnostic Signature Challenge," Bioinformatics, vol. 29, No. 22, 2013, pp. 2892-2899.
Tarca, et al., "The prediction of early preeclampsia: Results from a longitudinal proteomics study," PLoS One, vol. 14, No. 6, 2019, 34 pages.

*Primary Examiner* — Gary Counts
(74) *Attorney, Agent, or Firm* — Lee & Hayes P.C.; Tanya M. Harding

(57) ABSTRACT

Kits and methods to distinguish between false and true labor are provided. The kits and methods can utilize differences in abundance and/or differences in the rate of change in abundance of B7-H2, SORC2, TF, C1-Esterase Inhibitor, Ran, IMDH1 and/or PGAM1, as markers of true labor.

19 Claims, 14 Drawing Sheets

Specification includes a Sequence Listing.

FIG. 1

MRLGSPGLLFLLFSSLRADTQEKEVRAMVGSDVELSCACPEGSRFDLNDVYVYWQTS
ESKTVVTYHIPQNSSLENVDSRYRNRALMSPAGMLRGDFSLRLFNVTPQDEQKFHCL
VLSQSLGFQEVLSVEVTLHVAANFSVPVVSAPHSPSQDELTFTCTSINGYPRPNVYWIN
KTDNSLLDQALQNDTVFLNMRGLYDVVSVLRIARTPSVNIGCCIENVLLQQNLTVGSQT
GNDIGERDKITENPVSTGEKNAATWSILAVLCLLVVVAVAIGWVCRDRCLQHSYAGAW
AVSPETELTGHV (SEQ ID NO: 1)

FIG. 2

MAHRGPSRASKGPGPTARAPSPGAPPPPRSPRSRPLLLLLLLLGACGAAGRSPEPGR
LGPHAQLTRVPRSPPAGRAEPGGGEDRQARGTEPGAPGPSPGPAPGPGEDGAPAA
GYRRWERAAPLAGVASRAQVSLISTSFVLKGDATHNQAMVHWTGENSSVILILTKYYH
ADMGKVLESSLWRSSDFGTSYTKLTLQPGVTTVIDNFYICPTNKRKVILVSSSLSDRDQ
SLFLSADEGATFQKQPIPFFVETLIFHPKEEDKVLAYTKESKLYVSSDLGKKWTLLQERV
TKDHVFWSVSGVDADPDLVHVEAQDLGGDFRYVTCAIHNCSEKMLTAPFAGPIDHGS
LTVQDDYIFFKATSANQTKYYVSYRRNEFVLMKLPKYALPKDLQIISTDESQVFVAVQE
WYQMDTYNLYQSDPRGVRYALVLQDVRSSRQAEESVLIDILEVRGVKGVFLANQKIDG
KVMTLITYNKGRDWDYLRPPSMDMNGKPTNCKPPDCHLHLHLRWADNPYVSGTVHT
KDTAPGLIMGAGNLGSQLVEYKEEMYITSDCGHTWRQVFEEEHHILYLDHGGVIVAIKD
TSIPLKILKFSVDEGLTWSTHNFTSTSVFVDGLLSEPGDETLVMTVFGHISFRSDWELV
KVDFRPSFSRQCGEEDYSSWELSNLQGDRCIMGQQRSFRKRKSTSWCIKGRSFTSAL
TSRVCECRDSDFLCDYGFERSSSSESSTNKCSANFWFNPLSPPDDCALGQTYTSSLG
YRKVVSNVCEGGVDMQQSQVQLQCPLTPPRGLQVSIQGEAVAVRPGEDVLFVVRQE
QGDVLTTKYQVDLGDGFKAMYVNLTLTGEPIRHRYESPGIYRVSVRAENTAGHDEAVL
FVQVNSPLQALYLEVVPVIGLNQEVNLTAVLLPLNPNLTVFYWWIGHSLQPLLSLDNSV
TTRFSDTGDVRVTVQAACGNSVLQDSRVLRVLDQFQVMPLQFSKELDAYNPNTPEW
REDVGLVVTRLLSKETSVPQELLVTVVKPGLPTLADLYVLLPPPRPTRKRSLSSDKRLA
AIQQVLNAQKISFLLRGGVRVLVALRDTGTAEQLGGGGGYWAVVVLFVIGLFAAGAFI
LYKFKRKPGRTVYAQMHNEKEQEMTSPVSHSEDVQGAVQGNHSGVVLSINSREMH
SYLVS (SEQ ID NO: 2)

FIG. 3

METPAWPRVPRPETAVARTLLLGWVFAQVAGASGTTNTVAAYNLTWKSTNFKTILEW
EPKPVNQVYTVQISTKSGDWKSKCFYTTDTECDLTDEIVKDVKQTYLARVFSYPAGNV
ESTGSAGEPLYENSPEFTPYLETNLGQPTIQSFEQVGTKVNVTVEDERTLVRRNNTFL
SLRDVFGKDLIYTLYYWKSSSSGKKTAKTNTNEFLIDVDKGENYCFSVQAVIPSRTVNR
KSTDSPVECMGQEKGEFREIFYIIGAVAFVVIILVIILAISLHKCRKAGVGQSWKENSPLN
VS (SEQ ID NO: 3)

FIG. 4

MASRLTLLTLLLLLLAGDRASSNPNATSSSSQDPESLQDRGEGKVATTVISKMLFVEPIL
EVSSLPTTNSTTNSATKITANTTDEPTTQPTTEPTTQPTIQPTQPTTQLPTDSPTQPTTG
SFCPGPVTLCSDLESHSTEAVLGDALVDFSLKLYHAFSAMKKVETNMAFSPFSIASLLT
QVLLGAGENTKTNLESILSYPKDFTCVHQALKGFTTKGVTSVSQIFHSPDLAIRDTFVNA
SRTLYSSSPRVLSNNSDANLELINTWVAKNTNNKISRLLDSLPSDTRLVLLNAIYLSAKW
KTTFDPRKTRMEPFHFKNSVIKVPMMNSKKYPVAHFIDQTLKAKVGQLQLSHNLSLVIL
VPQNLKHRLEDMEQALSPSVFKAIMEKLEMSKFQPTLLTLPRIKVTTSQDMLSIMEKLE
FFDFSYDLNLCGLTEDPDLQVSAMQHTVLELTETGVEAAAASAISVARTLLVFEVQQP
FLFVLWDQQHKFPVFMGRVYDPRA (SEQ ID NO: 4)

FIG. 5

MAAQGEPQVQFKLVLVGDGGTGKTTFVKRHLTGEFEKKYVATLGVEVHPLVFHTNRG
PIKFNVWDTAGQEKFGGLRDGYYIQAQCAIIMFDVTSRVTYKNVPNWHRDLVRVCENI
PIVLCGNKVDIKDRKVKAKSIVFHRKKNLQYYDISAKSNYNFEKPFLWLARKLIGDPNLE
FVAMPALAPPEVVMDPALAAQYEHDLEVAQTTALPDEDDDL (SEQ ID NO: 5)

FIG. 6

MADYLISGGTGYVPEDGLTAQQLFASADDLTYNDFLILPGFIDFIADEVDLTSALTRKITL
KTPLISSPMDTVTEADMAIAMALMGGIGFIHHNCTPEFQANEVRKVKNFEQGFITDPVV
LSPSHTVGDVLEAKMRHGFSGIPITETGTMGSKLVGIVTSRDIDFLAEKDHTTLLSEVMT
PRIELVVAPAGVTLKEANEILQRSKKGKLPIVNDCDELVAIIARTDLKKNRDYPLASKDS
QKQLLCGAAVGTREDDKYRLDLLTQAGVDVIVFHSSQGNSVYQIAMVHYIKQKYPHLQ
VIGGNVVTAAQAKNLIDAGVDGLRVGMGCGSICITQEVMACGRPQGTAVYKVAEYAR
RFGVPIIADGGIQTVGHVVKALALGASTVMMGSLLAATTEAPGEYFFSDGVRLKKYRG
MGSLDPMEKSSSSQKRYFSEGDKVKIAQGVSGSIQDKGSIQKFVPYLIAGIQHGCQDIG
ARSLSVLRSMMYSGELKFEKRTMSPQIEGGVHGLHSYEKRLY (SEQ ID NO: 6)

FIG. 7

MAAYKLVLIRHGESAWNLENRFSGWYDADLSPAGHEEAKRGGQALRDAGYEFDICFT
SVQKRAIRTLWTVLDAIDQMWLPVVRTWRLNERHYGGLTGLNKAETAAKHGEAQVKI
WRRSYDVPPPPMEPDHPFYSNISKDRRYADLTEDQLPSCESLKDTIARALPFWNEEIV
PQIKEGKRVLIAAHGNSLRGIVKHLEGLSEEAIMELNLPTGIPIVYELDKNLKPIKPMQFL
GDEETVRKAMEAVAAQGKAKK (SEQ ID NO: 7)

FIG. 8

|  | Dataset 1 | | | Dataset 2 |
|---|---|---|---|---|
|  | Term delivery without labor (n=20) | Term delivery with labor (n=20) | P value | Term delivery without labor (n=50) |
| Maternal age (years) | 24.5 (21.3-28.3) | 24.5 (20.3-26.0) | 0.81 | 24 (20-28) |
| Pre-pregnant body mass index (kg/m$^2$) | 26.0 (23.6-31.7) | 24.8 (21.0-32.5) | 0.16 | 27.6 (23.5-34.8) |
| Race (%) | | | 0.27 | |
| • African American | 95% (19) | 80% (16) | | 49 (98%) |
| • Caucasian | 0 | 10% (2) | | 1 (2%) |
| • Other | 5% (1) | 10% (2) | | |
| Nulliparity (%) | 20% (4) | 35% (7) | 0.29 | 30% (15) |
| Gestational age at venipuncture (weeks) | | | | |
| Gestational age at delivery (weeks) | 40.1 (39.3-40.4) | 39.1 (38.2-39.4) | <0.001 | 40.0 (39.0-40.8) |
| Route of delivery (%) | | | 0.002 | |
| • Vaginal delivery | 45% (9) | 90% (18) | | 30% (15) |
| • Cesarean delivery | 55% (11) | 10% (2) | | 70% (35) |
| Birthweight (grams) | 3473 (3237-3565) | 3235 (3030-3399) | 0.03 | 3393 (3101-3620) |

Data are presented as median (interquartile range) or percent (n)

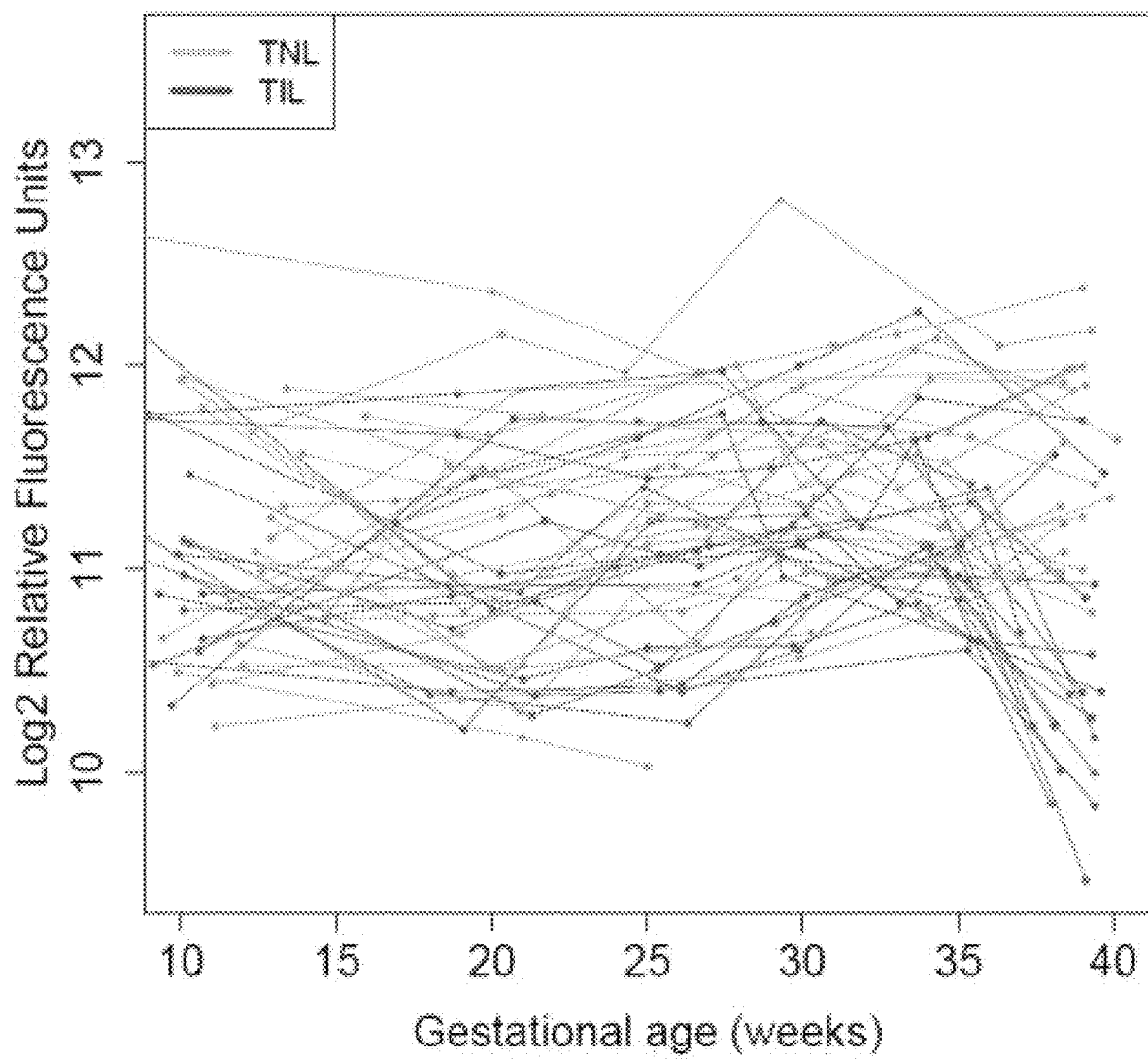

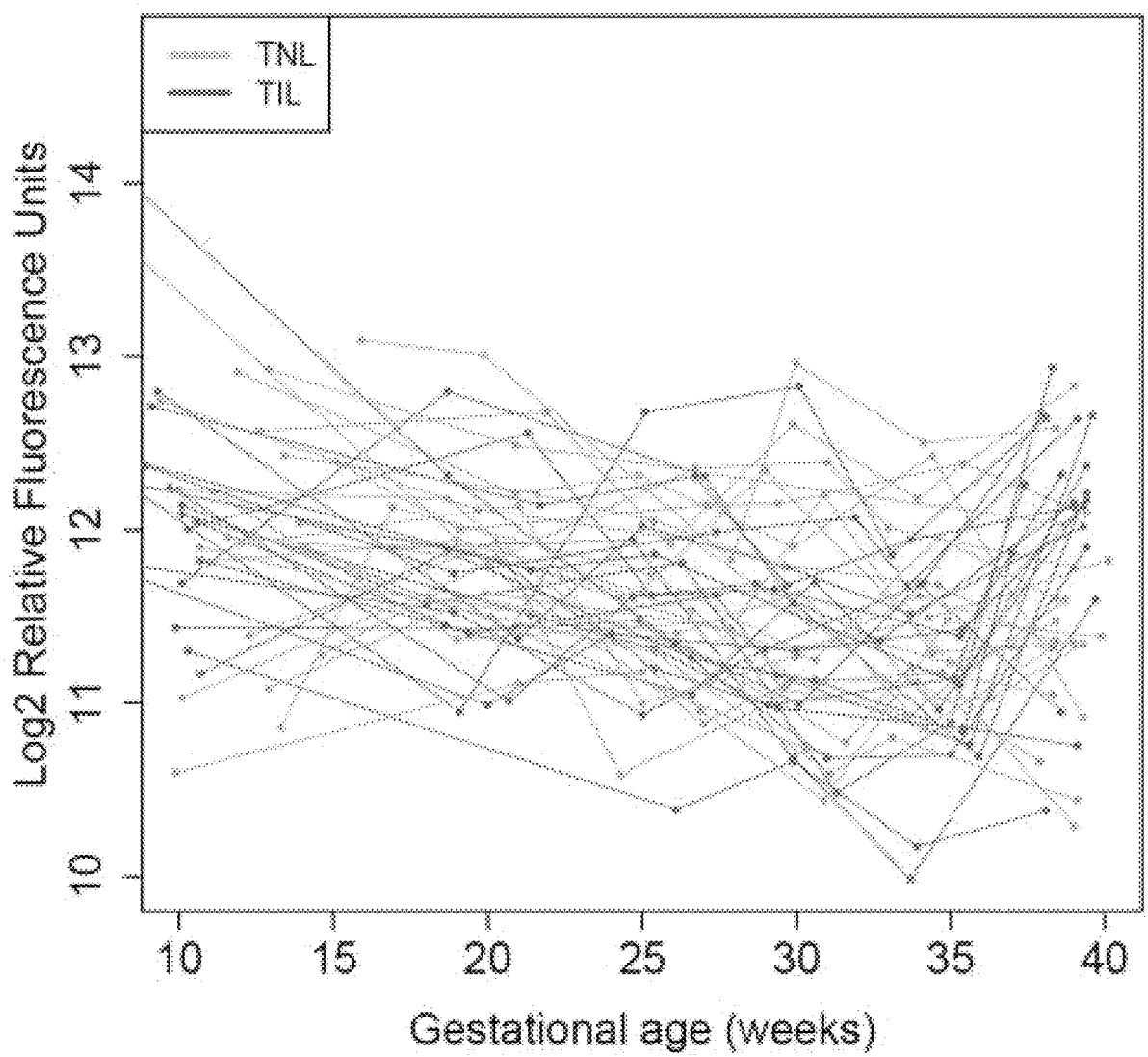

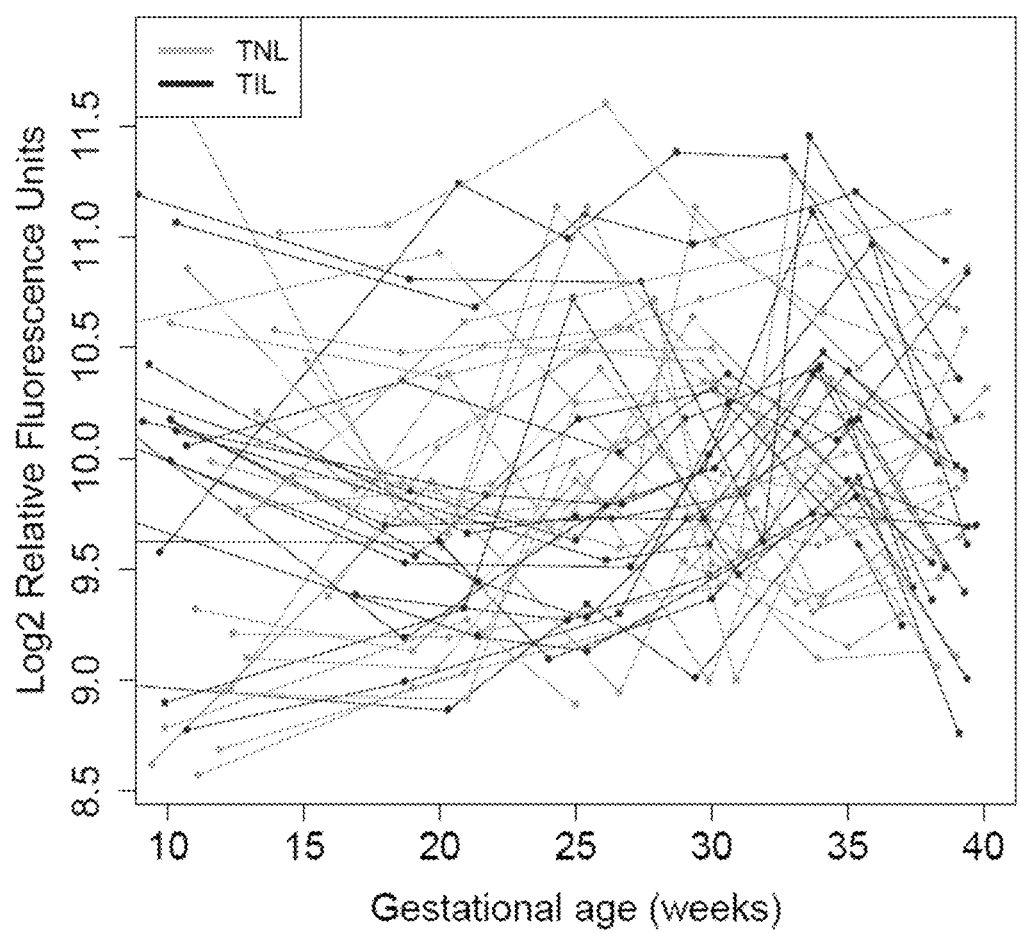

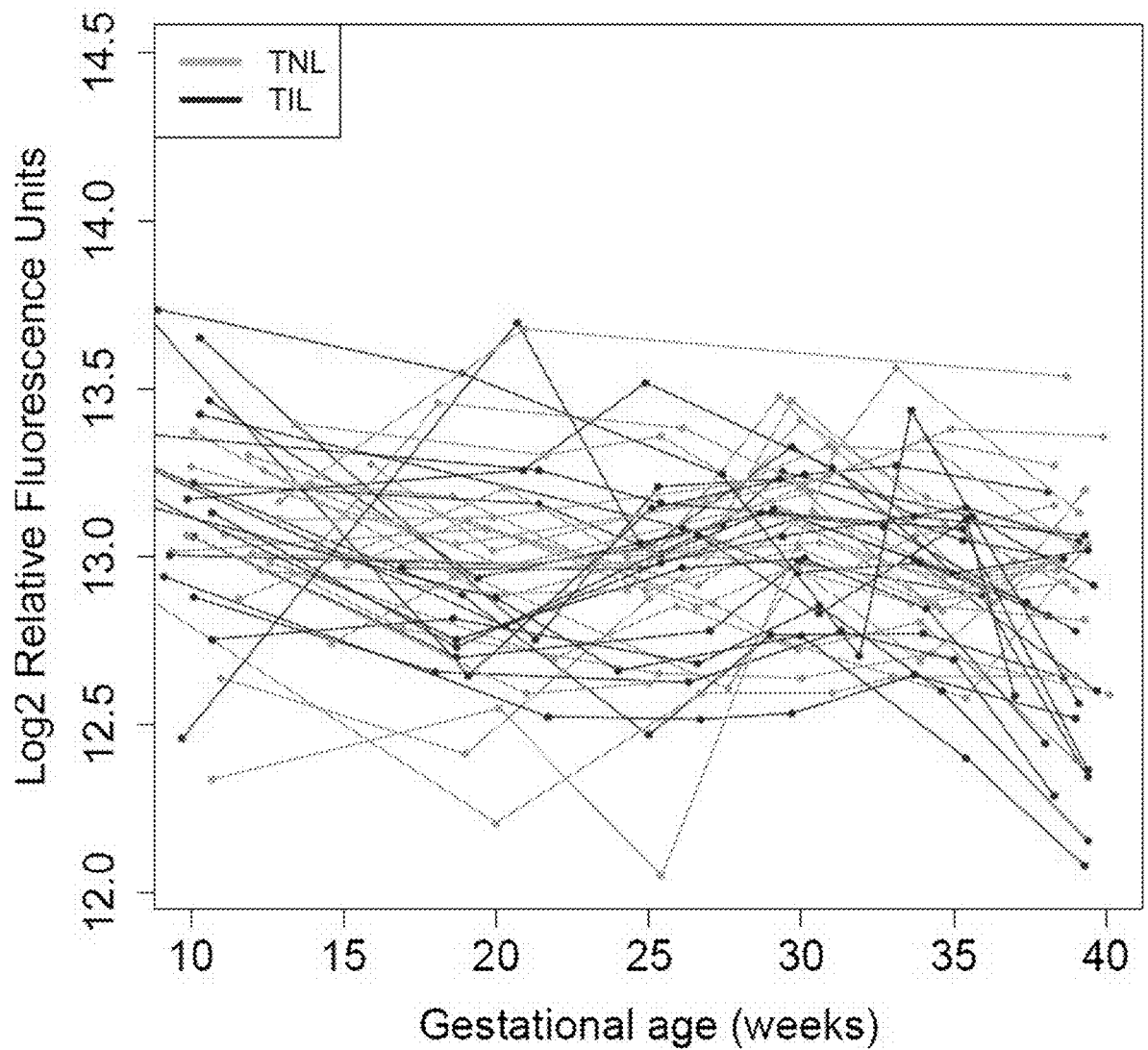

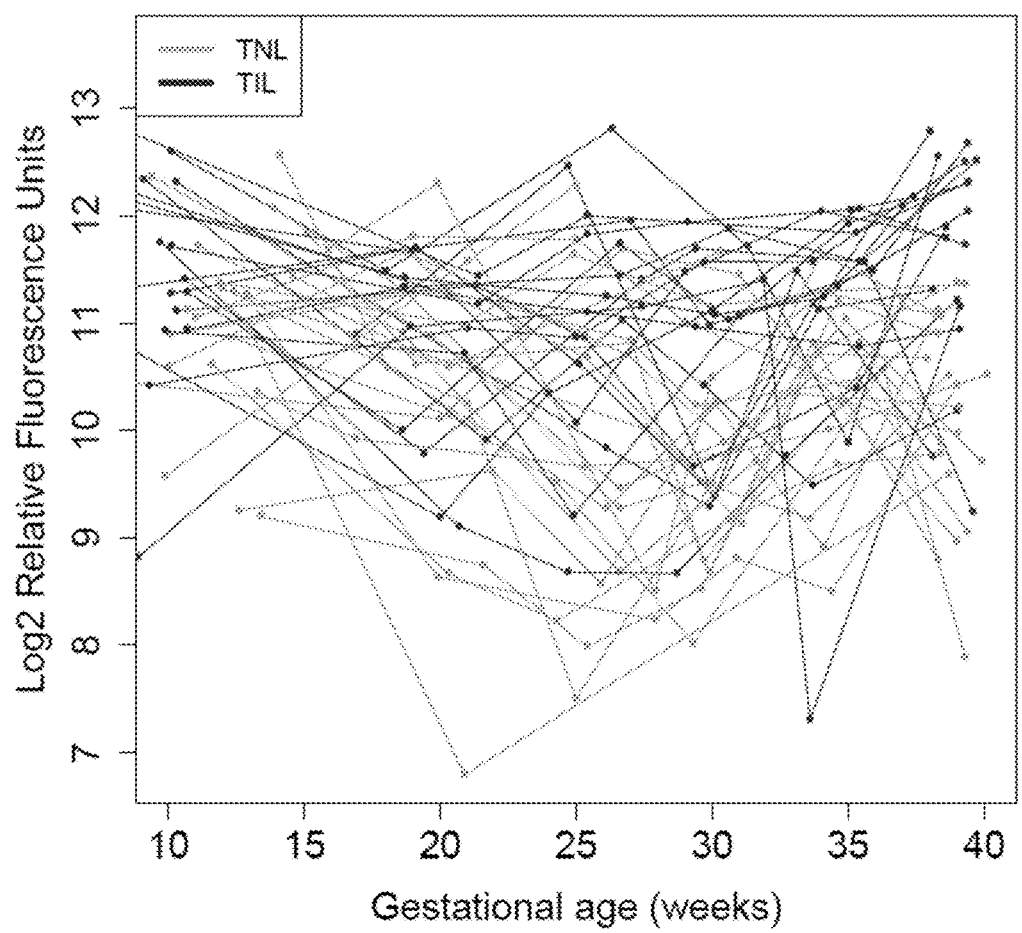

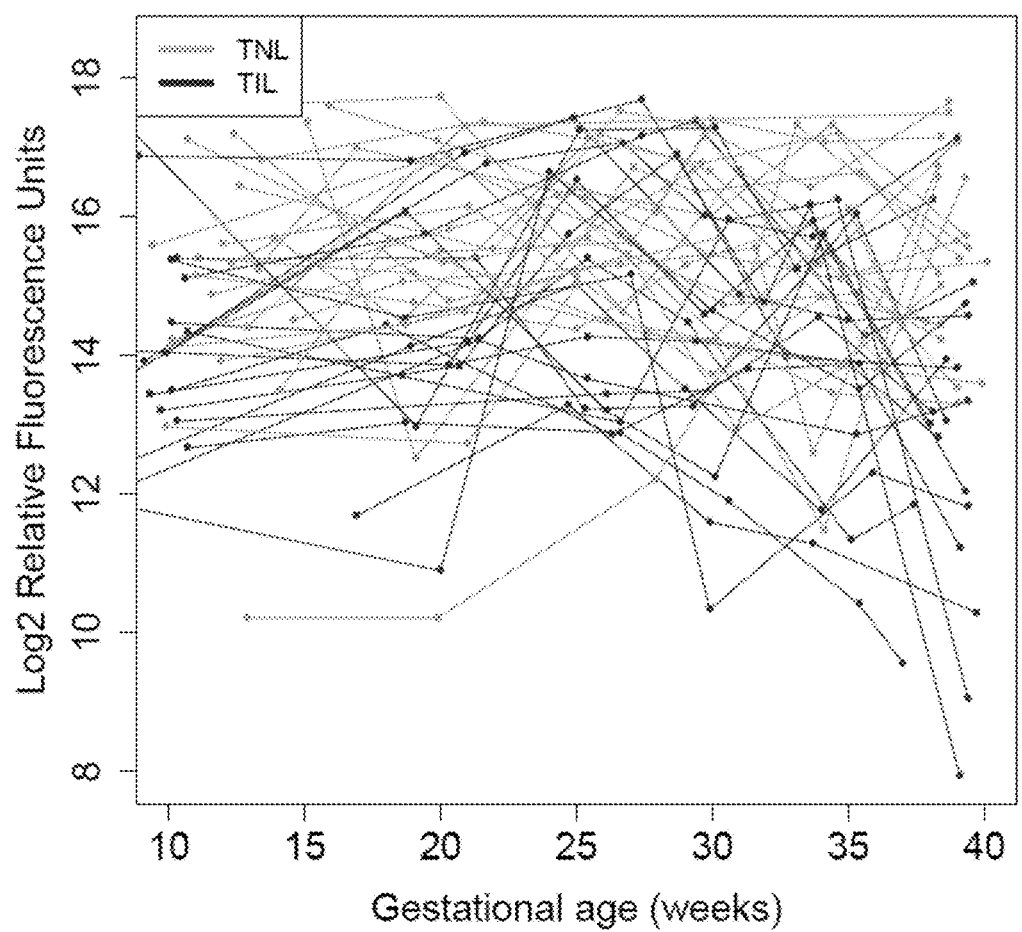

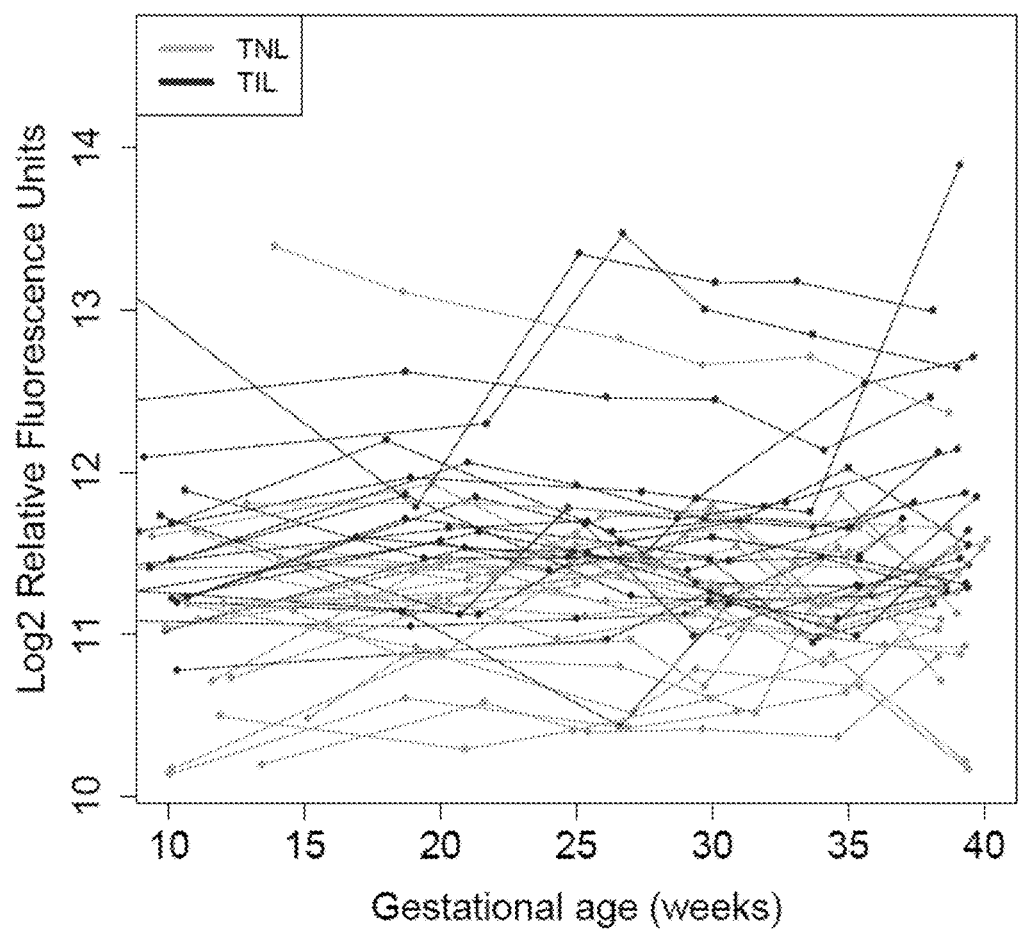

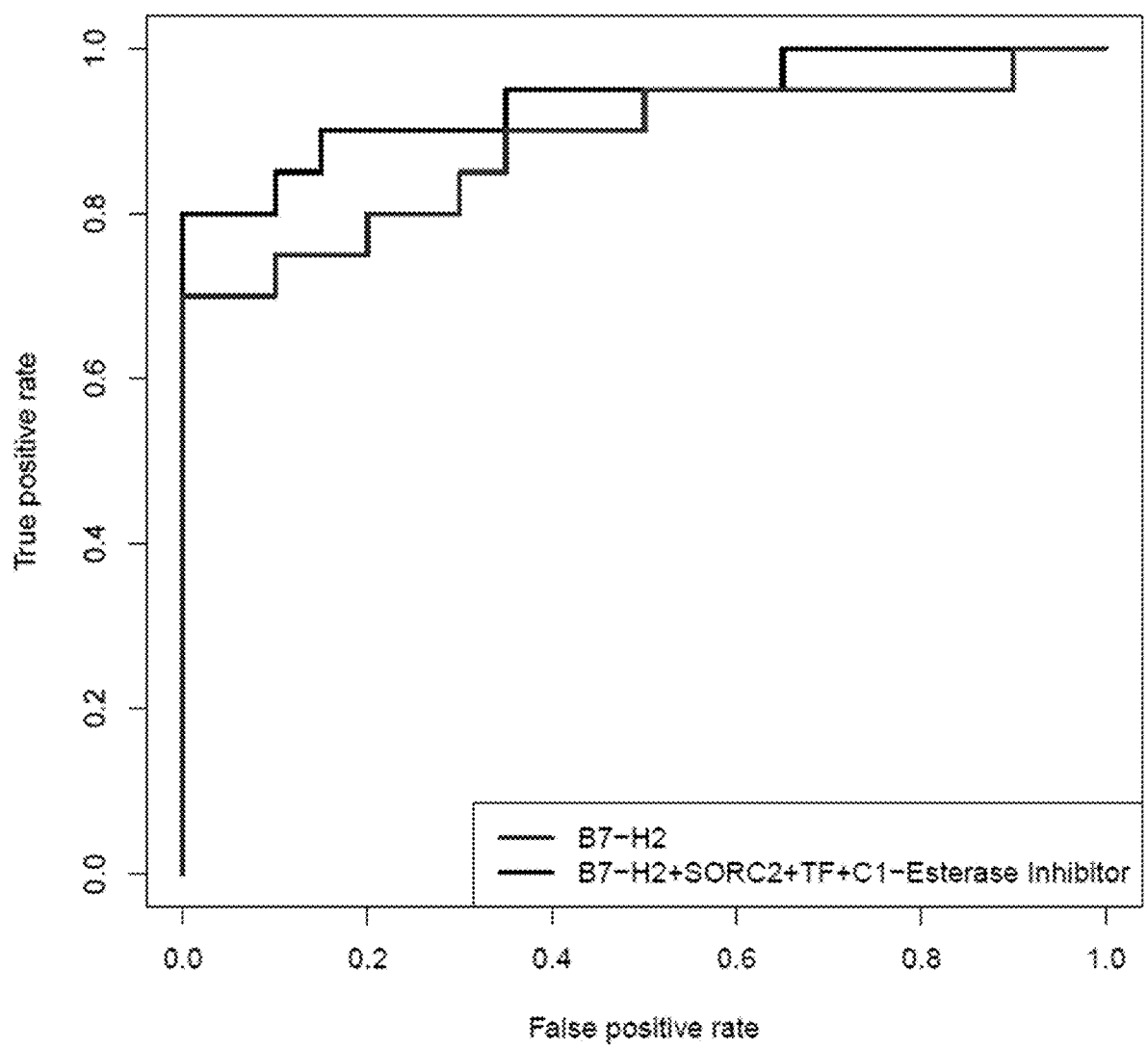

Score=$4.422 \cdot S_{(B7-H2)} -5.981 \cdot S_{(SORC2)} - 0.538 \cdot S_{(TF)} -0.033 \cdot S_{(C1-Esterase\ Inhibitor)} +1.314$
S=$(Abundance_{T2}-Abundance_{T1})/(GA_{T2}-GA_{T1})$
$T_1$= Second to last time point; $T_2$= Last time point

KITS AND METHODS TO DISTINGUISH FALSE LABOR AND TRUE LABOR

CROSS REFERENCE TO RELATED APPLICATIONS

This application is a divisional of U.S. patent application Ser. No. 15/773,980, filed May 4, 2018, now U.S. Pat. No. 11,204,354; which is the U.S. National Phase Application of International Patent Application No. PCT/US2016/060819, which was filed on Nov. 7, 2016; which claims priority to and the benefit of the earlier filing date of U.S. Provisional Patent Application No. 62/251,517 filed on Nov. 5, 2015. Each of these earlier filed applications is incorporated herein by reference in its entirety as if fully set forth herein.

STATEMENT REGARDING FEDERALLY SPONSORED RESEARCH

This invention was made with government support under HHSN275201300006C awarded by the National Institutes of Health. The government has certain rights in the invention.

FIELD OF THE DISCLOSURE

Kits and methods to distinguish between false and true labor are provided. The kits and methods can utilize differences in the rate of change in abundance of B7-H2, SORC2, TF, and C1-Esterase Inhibitor across at least two measures during pregnancy, as markers of true labor. Additionally, the kits and methods can utilize changes in abundance of TF, Ran, IMDH1, and PGAM1, as markers of true labor.

BACKGROUND OF THE DISCLOSURE

The diagnosis of labor is one of the great challenges in obstetrical care and is always retrospective. Despite the progress of modern medicine, clinical symptoms (i.e. pain, leakage of amniotic fluid or expulsion of the cervical mucus plug) and cervical examination (i.e. Bishop Score) are still the primary criteria used to diagnose true labor. Yet, the Bishop score which is predominantly influenced by the degree of cervical dilatation and effacement is a poor predictor of true labor (Rozeboom et al., The Journal of reproductive medicine 1989; 34(4):285-8; Lim et al., Journal of clinical ultrasound: JCU 1992; 20(9):599-603; and Berghella et al., American journal of obstetrics and gynecology 1997; 177(4):723-30).

Overdiagnosis of labor occurs at full-term (during or after the 37$^{th}$ week of gestation) as well as preterm (before the 37$^{th}$ week of gestation). The imprecise diagnosis of labor at full-term or preterm can lead to an increase in hospitalization, psychological stress, cost and unnecessary medical interventions such as analgesia and labor induction or augmentation. The increased risk of labor induction and augmentation caused by misdiagnosis of labor can be particularly harmful if the misdiagnosis occurs during preterm, when the fetus is not yet fully developed. Yet, overdiagnosis of labor occurs in up to 40% of women presenting with preterm labor symptoms. Currently, there are no diagnostic tests to determine if a woman is having true versus false labor.

SUMMARY OF THE DISCLOSURE

The present disclosure describes kits and methods to distinguish true from false labor, with specificity as high as 94%. The high specificity of these labor tests means that in the presence of a negative test result, patients are highly unlikely to deliver. Therefore, unnecessary hospital admissions, medical interventions, and costs can be avoided.

The current disclosure provides that seven biomarkers that can be found in maternal blood plasma predict the onset of true labor (also referred to as active labor) or show that true labor is in progress. These markers include:

| Name | UniProt ID |
| --- | --- |
| ICOS Ligand (B7-H2) | O75144 |
| VPS10 Domain Containing Receptor SorCS2 (SORC2) | Q96PQ0 |
| Tissue Factor (TF) | P13726 |
| Plasma Protease C1 Inhibitor (C1-Esterase Inhibitor) | P05155 |
| Ras-related Nuclear protein (Ran) | P62826 |
| Inosine-5'-monophosphate dehydrogenase (IMDH1) | P20839 |
| Phosphoglycerate mutase 1 (PGAM1) | P18669 |

More particularly, two models for the prediction of true labor have been developed. In the first model, differences in the rate of change of protein abundance of four markers (B7-H2, SORC2 TF, and C1-Esterase Inhibitor) across at least two measures are indicative of true labor, or a lack thereof. In the second model, changes in the abundance of four markers (TF, Ran, IMDH1, and PGAM1) at patient admission are indicative of true labor, or a lack thereof. The two models can be used individually or in combination.

BRIEF DESCRIPTION OF THE DRAWINGS

FIG. 1. Exemplary sequence of ICOS Ligand (B7-H2; SEQ ID NO: 1).

FIG. 2. Exemplary sequence of VPS10 Domain Containing Receptor SorCS2 (SORC2: SEQ ID NO: 2).

FIG. 3. Exemplary sequence of Tissue Factor (TF; SEQ ID NO: 3).

FIG. 4. Exemplary sequence of Plasma Protease C1 Inhibitor (C1-Esterase; Inhibitor; SEQ ID NO: 4).

FIG. 5. Exemplary sequence of Ras-related Nuclear protein (Ran) (SEQ ID NO: 5).

FIG. 6. Exemplary sequence of Inosine-5'-monophosphate dehydrogenase (IMDH1; SEQ ID NO: 6).

FIG. 7. Exemplary sequence of Phosphoglycerate mutase 1 (PGAM1; SEQ ID NO: 7).

FIG. 8. Clinical characteristics of the study population.

FIGS. 9A-9B. Longitudinal protein abundance profiles for TF (FIG. 9A) and B7-H2 (FIG. 9B) in 20 patients who delivered with spontaneous labor at term (TIL, gray) and 20 patients who delivered without spontaneous labor at term (TNL, light gray). Protein abundance is expressed in relative fluorescence units.

FIGS. 10A-10E. Longitudinal protein abundance profiles for SORC2 (FIG. 10A), C1-Esterase Inhibitor (FIG. 10B), Ran (FIG. 10C), PGAM1 (FIG. 10D), and IMDH1 (FIG. 10E) in 20 patients who delivered with spontaneous labor at term (TIL, dark gray) and 20 patients who delivered without spontaneous labor at term (TNL, light gray). Protein abundance is expressed in relative fluorescence units.

FIG. 11. Receiver Operating Characteristic curves of a four-protein classifier (black) and for B7-H2 alone (gray) obtained when predicting spontaneous labor using the rate of change in protein abundance determined from two serial measurements taken between 33 and 40 weeks of gestation. Area under the ROC curve was 0.94 for the four proteins while B7-H2 alone achieved 0.88.

REFERENCE TO SEQUENCE LISTING

Figure 12:
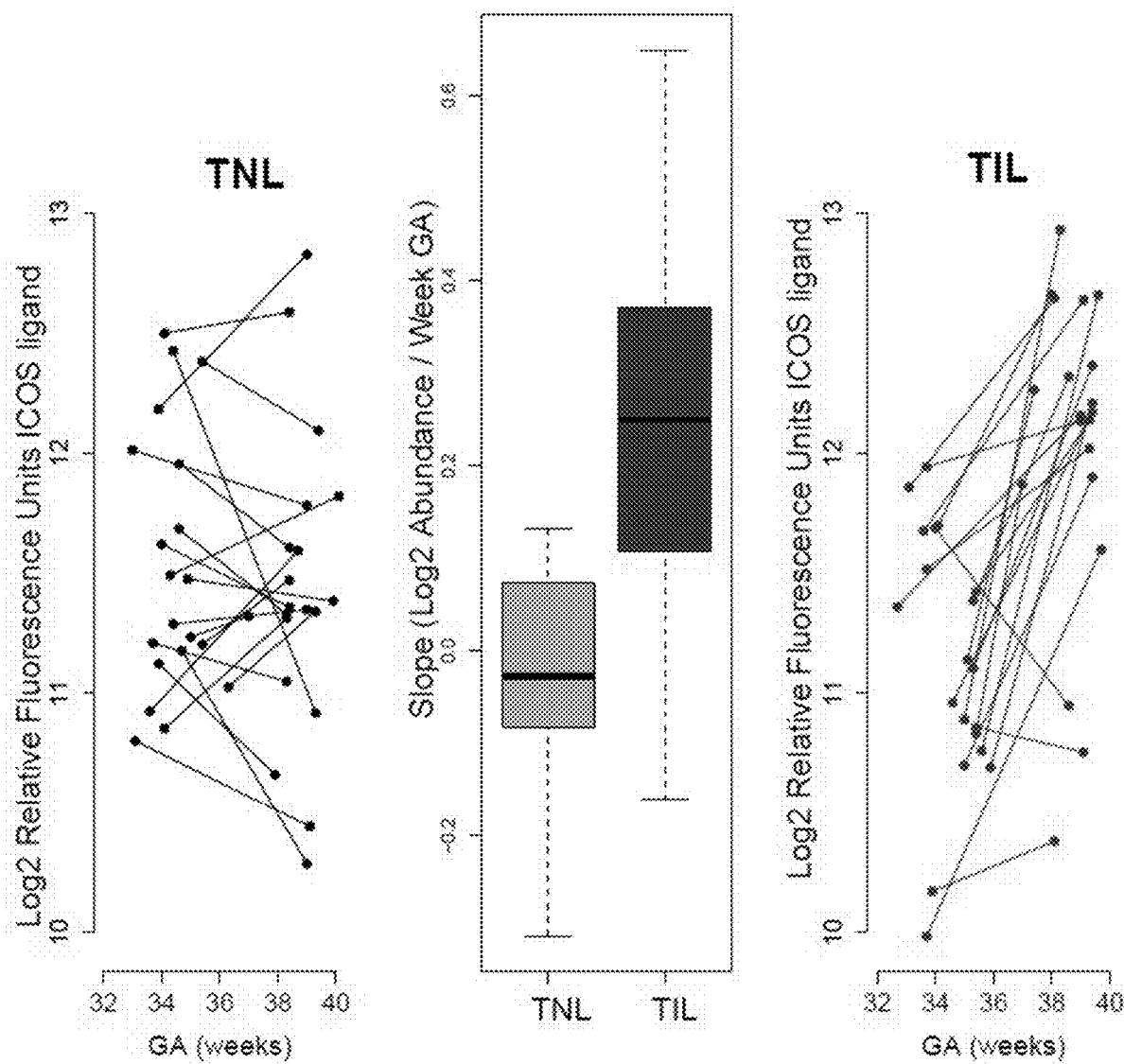
FIG. 12. B7-H2 protein abundance and slopes calculation. Left and right panels show B7-H2 protein abundance (log 2 of) in relative fluorescence units, as a function of gestational age at the last two samples in 20 TIL and 20 TNL patients. The middle panel shows a boxplot representation of the slopes defined as (log 2 abundance at last sample–log 2 abundance at second to last sample)/(GA at last sample–GA at second to last sample). The boxes represent the interquartile range, the thick line being the median value. Whiskers extend up to the extreme values if not more than 1.5 time the IQR. TIL=term in labor, TNL=term not in labor, GA=gestational age.

The amino acid sequences described herein are shown using standard letter abbreviations, as defined in 37 C.F.R. § 1.822. A computer readable text file, entitled "2L73589.txt (Sequence Listing.txt)" created on or about Nov. 10, 2021, with a file size of 28 KB, contains the Sequence Listing for this application and is hereby incorporated by reference in its entirety.

DESCRIPTION

What is Labor: During pregnancy the uterus undergoes two major processes, the first is a substantial growth that is characterized by hypertrophy and hyperplasia of the myometrium and the second process is the quiescence of the myometrium that is believed to be a balance between the hormonal effect of progesterone and the degree of stretching of the myometrial cells what is known as phase zero of parturition (or childbirth). The transition from quiescent to labor activates the common pathway of parturition, and includes myometrium contractions, cervical ripening (effacement and dilatation) and activation of the decidua and chorioamniotic membranes often presented as rupture of the membranes. However, these changes may sometimes be transient, for example, 40-60% of patients presenting with premature contractions will deliver at term. Even at term, a large fraction of patients may present with contractions and/or certain degree of cervical effacement and dilatation, but would not progress into active labor. The current diagnostic modalities for the identification of the labor process include physical examination of the uterus and the pelvis and tocometry. These modalities are not sensitive enough and often result in a false definition of labor, leading to unnecessary hospitalization and medical interventions that put the patient at increased risk for cesarean section (MacDorman et al., Clinics in perinatology 2008; 35(2):293-307; Gregory et al., American journal of perinatology 2012; 29(1):7-18). Recently, the use of transvaginal sonography for cervical length measurement with a cutoff of 1.5 cm has been proposed to be used for the differentiation between true and false labor in term patients. However this method had only 84% specificity and 67% sensitivity, a positive likelihood ratio of 4.2 and a negative likelihood ratio of 0.39 for the identification of true labor in patients at term (Kunzier et al., American journal of obstetrics and gynecology 2016(3): 372.e1-5). Thus, a robust and novel diagnostic tool to assist in the identification of patients who are truly going into labor is needed.

Biomarkers for Labor: Labor is a complex process characterized by systemic and local changes in inflammatory, hematologic, and hormonal processes. In recent years, high-dimensional biology was employed to identify the metabolome, transcriptome, and proteome of all the components of the common pathway of parturition.

In one metabolomic study of parturition, eighteen urine metabolites determined by gas chromatograph/mass spectrometry (GC/MS) and nuclear magnetic resonance spectroscopy (NMR) were found to be able to differentiate between women during labor and those before labor (Caboni et al., The journal of maternal-fetal & neonatal medicine 2014; 27 Suppl 2:4-12). In addition, the metabolomics analysis showed that the syntheses as well as degradation of ketone bodies were the most relevant biochemical pathways in urine samples from patients with labor.

Several transcriptome reports showed that spontaneous labor has a unique gene expression profile of the myometrium (e.g. Chan et al., The Journal of clinical endocrinology and metabolism 2002; 87(6):2435-41), cervix (e.g. Hassan et al., American journal of obstetrics and gynecology 2006; 195(3):778-86), and chorioamniotic membranes (e.g. Haddad et al., American journal of obstetrics and gynecology 2006; 195(2):394 e1-24) that differ from that of patients without labor.

Many studies have used proteomic methods to attempt to identify biomarkers for preterm labor, and other obstetrical complications. Proteomics is the large-scale analysis of proteins including their expression profiles, structures and functions. It is a technique that is frequently used for the development of biomarkers in clinical medicine. This is because it studies the final gene product (a specific protein) which is more complex and closer to biological function than the gene itself.

One proteomics study of parturition demonstrated a significant change in the proteomic profile of the cervical vaginal fluid in women prior to labor at term (Di Quinzio et al., Journal of proteome research 2008; 7(5):1916-21; Heng et al., Frontiers in physiology. 2015; 6:151). However, few studies have reported on different methods to distinguish true from false labor at term. Furthermore, the maternal plasma proteome prior to labor at term has not been reported thus far.

The present disclosure describes kits and methods to distinguish true from false labor, with specificity as high as 94%. The high specificity of these labor tests means that in the presence of a negative test result, patients are highly unlikely to deliver. Therefore, unnecessary hospital admissions, medical interventions, and costs can be avoided.

The current disclosure provides that measures of seven markers that can be found in maternal blood plasma can demonstrate that true labor is in process. These markers include:

| Name | UniProt ID |
|---|---|
| ICOS Ligand (B7-H2) | O75144 |
| VPS10 Domain Containing Receptor SorCS2 (SORC2) | Q96PQ0 |
| Tissue Factor (TF) | P13726 |
| Plasma Protease C1 Inhibitor (C1-Esterase Inhibitor) | P05155 |
| Ras-related Nuclear protein (Ran) | P62826 |

-continued

| Name | UniProt ID |
|---|---|
| Inosine-5'-monophosphate 1 dehydrogenase (IMDH1) | P20839 |
| Phosphoglycerate mutase 1 (PGAM1) | P18669 |

More particularly, two models for the prediction of true versus false labor have been developed. In the first model, differences in the rate of change of protein abundance of four markers (B7-H2, SORC2 TF, and C1-Esterase Inhibitor) across at least two measures are indicative of true labor, or a lack thereof. In the second model, changes in the abundance of four markers (TF, Ran, IMDH1, and PGAM1) are indicative of true labor, or a lack thereof.

The tests can be performed based on biological samples taken when women are admitted to the hospital due to an episode of suspected labor. Levels of the markers can be compared to a measure previously taken from the same woman, and changes in abundance (e.g., slope) can be calculated. In particular embodiments, a biological sample is plasma or serum. In particular embodiments, a biological sample may be obtained at an earlier timepoint in a pregnancy (e.g., the beginning of the third trimester) and when true labor is suspected, but not confirmed. In particular embodiments, a biological sample may be obtained at an earlier timepoint in a pregnancy (e.g., the beginning of the third trimester) and when false labor is suspected, but not confirmed.

In particular embodiments, the kits and methods are used to identify true labor when a pregnant female is experiencing symptoms of labor. Symptoms of labor can include cramps and back pain, diarrhea, lethargy, dilation of the cervix, and contractions. Contractions can be defined as the periodic tightening and relaxing of the uterine muscle. Contractions can be a sign of true labor, or can be associated with false labor.

In particular embodiments, the kits and methods to identify true labor include measuring B7-H2. B7 is a family of membrane proteins that are expressed by antigen presenting cells. B7 binds to proteins expressed on the surface of T cells and can either enhance or dampen activation of T cells upon engagement of a T cell receptor with its cognate antigen and major histocompatibility complex (MHC or human leukocyte antigen complex, HLA). There are several members of the B7 protein family including: B7-1, B7-2, B7-DC, and B7-H1 through H7. B7-H2 (also known as ICOSLG, B7RP1 and CD275) interacts with ICOS and/or CD28 expressed by T cells to provide a costimulatory signal to T cells, which can contribute to T cell activation upon T cell receptor engagement with an antigen/MHC complex. An exemplary sequence of human B7-H2 (UniProt ID O75144) is GenBank Accession number AF289028 (see FIG. 1, SEQ ID NO: 1).

In particular embodiments, the kits and methods to identify true labor include measuring SORC2. SORC2 (also known as SORCS2) is a member of the vacuolar protein sorting 10 (VPS10) domain-containing receptor proteins. In mammals, VPS10 family proteins such as SORC2 are predominantly expressed in the central nervous system. An exemplary sequence of human SORC2 (UniProt ID Q96PQ0) is GenBank Accession number NM_020777.2 (see FIG. 2, SEQ ID NO: 2).

In particular embodiments, the kits and methods to identify true labor include measuring TF. TF (also known as platelet tissue factor, factor III, thromboplastin and CD142) is a membrane protein that initiates blood coagulation, which can be caused by tissue damage or inflammation. TF is a member of the cytokine receptor protein family, which includes membrane proteins that have an extracellular domain that can bind to extracellular factors to initiate signaling, a transmembrane domain, and a cytosolic domain that can transmit a signal induced by an extracellular interaction. The extracellular domain of TF binds to factor VIIa to initiate a coagulation signaling cascade. Exemplary sequences of human TF (UniProt ID P13726) include GenBank Accession numbers J02931.1 and M16553 (see FIG. 3, SEQ ID NO: 3).

In particular embodiments, the kits and methods to identify true labor include measuring C1-Esterase Inhibitor. C1-Esterase Inhibitor (also known as C1-Inhibitor and Plasma Protease C1 Inhibitor) is a regulator of the complement pathway and can prevent spontaneous activation of complement. The complement pathway is part of the innate immune system and can cause destruction of cellular membranes leading to death of cells such as virus-infected cells, bacteria, and fungi. C1-Esterase Inhibitor is a member of the serpin protein family. Serpin proteins can irreversibly inhibit proteases by binding to and inducing a conformational change in the protease active site. C1-Esterase Inhibitor binds and irreversibly blocks the activity of the complement pathway proteases C1r and C1s. An exemplary sequence of human C1-Esterase Inhibitor (UniProt ID P05155) is GenBank Accession number M13690 (see FIG. 4, SEQ ID NO: 4).

In particular embodiments, the kits and methods to identify true labor include measuring Ran (also known as ARA24). Ran is a small GTPase that translocates RNA and proteins through the nuclear pore complex. Regulation of Ran-mediated transport through the nuclear pore complex is controlled by whether Ran is bound to GTP or GDP. An exemplary sequence of human Ran (UniProt ID P62826) is GenBank Accession number AF052578 (see FIG. 5, SEQ ID NO: 5).

In particular embodiments, the kits and methods to identify true labor include measuring IMDH1. IMDH1 is an enzyme that converts inosine-5'-monophosphate to xanthosine-5'-monophosphate, which is a rate limiting step in the production of guanine nucleotides, such as GMP, GDP, and GTP. An exemplary sequence of human IMDH1 (UniProt ID P20839) is GenBank Accession number J05272 (see FIG. 6, SEQ ID NO: 6).

In particular embodiments, the kits and methods to identify true labor include measuring PGAM1 (also known as PGAM-B). PGAM1 is an enzyme that catalyzes a step in glycolysis, specifically, the conversion of 3-phosphoglycerate (3PG) to 2-phosphoglycerate (2PG). An exemplary sequence of human PGAM1 (UniProt ID P18669) is GenBank Accession number J04173 (see FIG. 7, SEQ ID NO: 7).

B7-H2, SORC2, TF, C1-Esterase Inhibitor, Ran, IMDH1, and PGAM1 are "biomarkers" or "markers" in the context of the present disclosure. Biomarkers include the protein forms of the markers as well as associated nucleic acids, oligonucleotides, and metabolites, together with their related metabolites, mutations, isoforms, variants, polymorphisms, modifications, fragments, subunits, degradation products, elements, and other analytes or sample-derived measures. Biomarkers can also include mutated proteins, mutated nucleic acids, variations in copy numbers, and/or transcript variants. Biomarkers also encompass combinations of any one or more of the foregoing measurements, including temporal trends and differences. Particular embodiments of biomarkers include B7-H2 (SEQ ID NO: 1); SORC2 (SEQ ID NO: 2); TF (SEQ ID NO: 3); C1-Esterase Inhibitor (SEQ ID NO: 4); Ran (SEQ ID NO: 5); IMDH1 (SEQ ID NO: 6); and/or PGAM1 (SEQ ID NO: 7).

Protein expression patterns can be evaluated using any method that provides a quantitative measure and is suitable for evaluation of multiple markers extracted from samples. Exemplary methods include: ELISA sandwich assays, mass spectrometric detection, calorimetric assays, binding to a protein array (e.g., antibody array), or fluorescent activated cell sorting (FACS). Approaches can use labeled affinity reagents (e.g., antibodies, small molecules, etc.) that recognize epitopes of one or more protein products in an ELISA, antibody array, or FACS screen.

In particular embodiments, the true labor markers can be measured using immunoassay techniques. Immunoassays are laboratory procedures that utilize antibodies and/or antigens to detect a molecule. In particular embodiments, the true labor markers can be detected using antibody-based techniques. In particular embodiments, B7-H2 can be detected using an anti-B7-H2 antibody. An example of a commercially available anti-B7-H2 antibody is mouse-anti-B7-H22D3, available from BioLegend. In particular embodiments, SORC2 can be detected using an anti-SORC2 antibody. An example of a commercially available anti-SORC2 antibody is mouse anti-SORCS2 ab88330, available from Abcam. In particular embodiments, TF can be detected using an anti-TF antibody. An example of a commercially available anti-TF antibody is mouse anti-Tissue Factor ab48647, available from Abcam. In particular embodiments, C1-Esterase Inhibitor can be detected using an anti-C1-Esterase Inhibitor antibody. An example of a commercially available anti-C1 Esterase Inhibitor antibody is mouse anti-C1 Inactivator EPR8015, available from Abcam. In particular embodiments, Ran can be detected using an anti-Ran antibody. An example of a commercially available anti-Ran antibody is mouse anti-Ran ab11693, available from Abcam. In particular embodiments, IMDH1 can be detected using an anti-IMDH1 antibody. An example of a commercially available anti-IMDH1 antibody is rabbit anti-IMDPH1, available from ThermoFisher Scientific. PGAM1 can be detected using an anti-PGAM1 antibody. An example of a commercially available anti-PGAM1 Inhibitor antibody is rabbit polyclonal anti-PGAM1 ab96622, available from Abcam.

Protein detection can include detection of full-length proteins, protein fragments, mature proteins, pre-proteins, polypeptides, isoforms, mutations, variants, post-translationally modified proteins, and variants thereof, and can be detected in any suitable manner. Levels of biomarkers can be determined at the protein level, e.g., by measuring the serum levels of proteins. Such methods are well-known in the art and include, e.g., immunoassays based on antibodies to proteins encoded by the genes, aptamers, or molecular imprints. Any biological material can be used for the detection/quantification of the protein or its activity. Alternatively, a suitable method can be selected to determine the activity of proteins. Such assays include protease assays, kinase assays, phosphatase assays, and reductase assays, among many others.

Variants of the sequences disclosed and referenced herein are also included. Variants of peptides can include those having one or more conservative amino acid substitutions. As used herein, a "conservative substitution" involves a substitution found in one of the following conservative substitutions groups: Group 1: Alanine (Ala), Glycine (Gly), Serine (Ser), Threonine (Thr); Group 2: Aspartic acid (Asp), Glutamic acid (Glu); Group 3: Asparagine (Asn), Glutamine (Gln); Group 4: Arginine (Arg), Lysine (Lys), Histidine (His); Group 5: Isoleucine (Ile), Leucine (Leu), Methionine (Met), Valine (Val); and Group 6: Phenylalanine (Phe), Tyrosine (Tyr), Tryptophan (Trp).

Additionally, amino acids can be grouped into conservative substitution groups by similar function or chemical structure or composition (e.g., acidic, basic, aliphatic, aromatic, sulfur-containing). For example, an aliphatic grouping may include, for purposes of substitution, Gly, Ala, Val, Leu, and Ile. Other groups containing amino acids that are considered conservative substitutions for one another include: sulfur-containing: Met and Cysteine (Cys); acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information is found in Creighton (1984) Proteins, W.H. Freeman and Company.

Variants of the protein and nucleic acid sequences disclosed or referenced herein also include sequences with at least 70% sequence identity, 80% sequence identity, 85% sequence, 90% sequence identity, 95% sequence identity, 96% sequence identity, 97% sequence identity, 98% sequence identity, or 99% sequence identity to the protein and nucleic acid sequences disclosed or referenced herein and particularly including SEQ ID NOs:1-7.

"% sequence identity" or "% identity" refers to a relationship between two or more sequences, as determined by comparing the sequences. In the art, "identity" also means the degree of sequence relatedness between proteins or nucleic acid sequences as determined by the match between strings of such sequences. "Identity" (often referred to as "similarity") can be readily calculated by known methods, including those described in: Computational Molecular Biology (Lesk, A. M., ed.) Oxford University Press, NY (1988); Biocomputing: Informatics and Genome Projects (Smith, D. W., ed.) Academic Press, NY (1994); Computer Analysis of Sequence Data, Part I (Griffin, A. M., and Griffin, H. G., eds.) Humana Press, N J (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wis.). Multiple alignment of the sequences can also be performed using the Clustal method of alignment (Higgins and Sharp CABIOS, 5, 151-153 (1989)) with default parameters (GAP PENALTY=10, GAP LENGTH PENALTY=10). Relevant programs also include the GCG suite of programs (Wisconsin Package Version 9.0, Genetics Computer Group (GCG), Madison, Wis.); BLASTP, BLASTN, BLASTX (Altschul, et al., J. Mol. Biol. 215:403-410 (1990)); DNASTAR (DNASTAR, Inc., Madison, Wis.); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y.). Within the context of this disclosure it will be understood that where sequence analysis software is used for analysis, the results of the analysis are based on the "default values" of the program referenced. As used herein "default values" will mean any set of values or parameters which originally load with the software when first initialized.

Using sequence information provided by public database entries for the biomarkers described herein, expression of the biomarker can be detected and measured using techniques well-known to those of skill in the art. For example, nucleic acid sequences in the sequence databases that correspond to nucleic acids of biomarkers can be used to construct primers and probes for detecting and/or measuring biomarker nucleic acids. These probes can be used in, e.g., Northern or Southern blot hybridization analyses, ribonuclease protection assays, and/or methods that quantitatively amplify specific nucleic acid sequences. As another example, sequences from sequence databases can be used to construct primers for specifically amplifying biomarker sequences in, e.g., amplification-based detection and quantitation methods such as reverse-transcription based polymerase chain reaction (RT-PCR) and PCR. When alterations in gene expression are associated with gene amplification, nucleotide deletions, polymorphisms, post-translational modifications and/or mutations, sequence comparisons in test and reference populations can be made by comparing relative amounts of the examined DNA sequences in the test and reference populations.

A number of methods for obtaining expression data can be used singly or in combination for determining expression patterns and profiles in the context of the present disclosure. For example, DNA and RNA expression patterns can be evaluated by northern analysis, PCR, RT-PCR, quantitative real-time RT-PCR analysis with TaqMan assays, FRET detection, monitoring one or more molecular beacon, hybridization to an oligonucleotide array, hybridization to a cDNA array, hybridization to a polynucleotide array, hybridization to a liquid microarray, hybridization to a microelectric array, molecular beacons, cDNA sequencing, clone hybridization, cDNA fragment fingerprinting, serial analysis of gene expression (SAGE), subtractive hybridization, differential display and/or differential screening.

Gene expression changes can be related to epigenetic variations (e.g. DNA methylation). Epigenetic regulation mechanisms do not involve a change to the DNA sequence. Instead, epigenetic variations include covalent modification of DNA, RNA, and the proteins associated with DNA. These in turn can result in changes to the conformation of DNA and accessibility of regulators to the DNA. Such changes cannot be identified simply by gene sequencing. Janssen, et al., Particle and Fibre Toxicology, 10:22 (2013) studied methylation in placental tissue using methods published by Tabish, et al., *PLoS ONE* 2012, 7:e34674 and by Godderis, et al., Epigenomics 4:269-277 (2012). MS-MLPA (Methylation-specific Multiplex ligation-dependent probe amplification) can be used to study methylation status of specific genes, for example in Proctor, et al., Clin. Chem. 52:1276-1283 (2006). Materials and methods for MS-MLPA as used in published studies can be obtained from MRC-Holland, Amsterdam, The Netherlands. Additional methods are reviewed and compared in Shen, et al., Curr. Opin. Clin. Nutr. Metab. Care. 10:576-81 (2007); Gu et al., Nature Methods 7:133-138 (2010); Bock et al., Nature Biotech. 28:1106-1114 (2010); and Harris et al., Nature Biotech. 28:1097-1105 (2010).

In particular embodiments, the kits and methods to distinguish between false and true labor include use of an array to measure markers. A variety of solid phase arrays can also be employed to determine expression patterns. Exemplary formats include membrane or filter arrays (e.g., nitrocellulose, nylon), pin arrays, and bead arrays (e.g., in a liquid "slurry"). Essentially any solid support capable of withstanding the reagents and conditions necessary for performing the particular expression assay can be utilized. For example, functionalized glass, silicon, silicon dioxide, modified silicon, any of a variety of polymers, such as (poly)tetrafluoroethylene, (poly)vinylidenedifluoride, polystyrene, polycarbonate, or combinations thereof can all serve as the substrate for a solid phase array.

In particular embodiments, arrays can include "chips" composed, e.g., of one of the above-specified materials. Polynucleotide probes, e.g., RNA or DNA, such as cDNA, synthetic oligonucleotides, and the like, or binding proteins such as antibodies or antigen-binding fragments or derivatives thereof, that specifically interact with expression products of individual components of the candidate library are affixed to the chip in a logically ordered manner, i.e., in an array. In addition, any molecule with a specific affinity for either the sense or anti-sense sequence of the marker nucleotide sequence (depending on the design of the sample labeling), can be fixed to the array surface without loss of specific affinity for the marker and can be obtained and produced for array production, for example, proteins that specifically recognize the specific nucleic acid sequence of the marker, ribozymes, peptide nucleic acids (PNA), or other chemicals or molecules with specific affinity.

Detailed discussion of methods for linking nucleic acids and proteins to a chip substrate, are found in, e.g., U.S. Pat. Nos. 5,143,854; 6,087,112; 5,215,882; 5,707,807; 5,807, 522; 5,958,342; 5,994,076; 6,004,755; 6,048,695; 6,060, 240; 6,090,556; and 6,040,138.

Microarray expression may be detected by scanning the microarray with a variety of laser or CCD-based scanners, and extracting features with software packages, for example, Imagene (Biodiscovery, Hawthorne, Calif.), Feature Extraction Software (Agilent), Scanalyze (Eisen, M. 1999. SCANALYZE User Manual; Stanford Univ., Stanford, Calif. Ver 2.32), or GenePix (Axon Instruments).

"Measuring" includes determining, assessing, calculating, and/or analyzing a value or set of values associated with a sample by measurement of marker (i.e., analyte) levels in the sample. "Determining" may further include comparing levels against constituent levels in a sample or set of samples from the same subject or other subject(s). The B7-H2, SORC2, TF, C1-Esterase Inhibitor, Ran, IMDH1, PGAM1 and/or other biomarkers of the present disclosure can be determined by any of various conventional methods known in the art.

In particular embodiments, quantitative data obtained for the markers of interest and other dataset components can be subjected to an analytic process with chosen parameters. The parameters of the analytic process may be those disclosed herein or those derived using the guidelines described herein. The analytic process used to generate a result may be any type of process capable of providing a result useful for classifying a sample, for example, comparison of the obtained dataset with a reference dataset, a linear algorithm, a quadratic algorithm, a decision tree algorithm, or a voting algorithm. The analytic process may set a threshold for determining the probability that a sample belongs to a given class (false labor or true labor). The probability preferably is at least 50%, or at least 60%, or at least 70%, or at least 80%, or at least 90% or higher. For example, particular embodiments utilize the formula and classification scale described in FIG. 13.

A "dataset" as used herein is a set of numerical values resulting from evaluation of a sample (or population of samples) under a desired condition. The values of the dataset can be obtained, for example, by experimentally obtaining measures from a sample and constructing a dataset from these measurements; or alternatively, by obtaining a dataset from a service provider such as a laboratory, or from a database or a server on which the dataset has been stored.

In particular embodiments of the present disclosure, a dataset of values is determined by measuring biomarkers from a non-pregnant subject or a pregnant subject who is not in labor. Datasets can be used by an interpretation function to derive a true labor score, which can provide a quantitative measure of likelihood that a subject is in true labor.

The sensitivity of a diagnostic measure is also referred to as the true positive rate, or the recall in some fields. It denotes the proportion of positive results (true labor occurring) that are correctly identified as such. The specificity of a diagnostic measure is also referred to as the true negative rate. It denotes the proportion of negatives that are correctly identified as such (false labor occurring).

In particular embodiments, the kits and methods disclosed herein have at least a 59% sensitivity and a 100% specificity. In particular embodiments, the kits and methods disclosed herein have at least a 75% sensitivity and a 100% specificity. In particular embodiments, the kits and methods disclosed herein true labor is identified with a specificity of 80% or greater, 81% or greater, 82% or greater, 83% or greater, 84% or greater, 85% or greater, 86% or greater, 87% or greater, 88% or greater, 89% or greater, 90% or greater, 91% or greater, 92% or greater, 93% or greater, 94% or greater, 95% or greater, 96% or greater, 97% or greater, 97% or greater, 98% or greater or 99% or greater.

A used herein, the term "change of abundance" with regard to changes in the marker levels can refer to an increase of more than 20%, more than 30%, more than 40%, more than 50%, more than 60%, more than 70%, more than 80%, more than 90%, more than 100%, more than 150%, or more than 200% compared to a reference level. In particular embodiments, "change of abundance" measures can be evaluated independently against a reference level without consideration of earlier comparisons in the same subject. In particular embodiments, "change of abundance" can refer to an increase of at least 1.5 times over a previous measure or as compared to a particular population reference level.

As used herein, "unchanged" measures are evaluated in relation to a previous comparison in the same subject and denote a failure to achieve a statistically significant change in a score towards or away from a reference level in the particular subject.

In particular embodiments, the amount of the biomarker(s) can be measured in a sample and used to derive a true labor score, which true labor score is then compared to a "reference level". Reference levels can include "normal", "control", "non-labor" or "false labor" levels or values, defined according to, e.g., discrimination limits or risk defining thresholds, in order to define cut-off points and/or abnormal values for true labor. The reference level then is the level of one or more biomarkers or combined biomarker indices typically found in a subject who is not in true labor. Other terms for "reference levels" include "index," "baseline," "standard," "pre-labor", etc. Such normal levels can vary, based on whether a biomarker is used alone or in a formula combined with other biomarkers to output a score. Alternatively, the reference level can be a database of biomarker patterns from previously tested subjects who did not go into labor over a clinically relevant time period. Reference levels can also be derived from, e.g., a control subject or population whose time of onset of labor is known. In particular embodiments, the reference value can be derived from one or more subjects who did not experience an onset of spontaneous labor, such a patient who underwent elective cesarean delivery. In particular embodiments, reference levels can be derived from the patient undergoing a true labor score analysis, wherein the reference level samples are obtained from said patient at a previous time-point.

In particular embodiments, "reference level" can refer to a standardized value for the markers which represents a level not associated with onset of labor. The reference level can be a universal reference level which is useful across a variety of testing locations or can be a reference level specific for the testing location and specific immunoassay used to measure the true labor markers. In particular embodiments, the reference levels of the true labor markers and/or reference weighted score is derived from (i) an individual; (ii) a group of individuals; (iii) a subject before pregnancy; or (iv) a pregnant subject not yet in labor; wherein the samples are obtained at time-points when each individual was not in true labor. In particular embodiments, the subject whose samples are used to obtain a reference level can be different from the subject who is being tested for true labor. In particular embodiments, the subject whose samples are used to obtain a reference level can be the same subject who is being tested for true labor. When the reference level is based on samples collected from the same subject, reference level samples can be collected at earlier time-points, either before pregnancy or at earlier time-points during pregnancy.

In particular embodiments, the term "rate of change of abundance" can refer to a rate of change over time, or a slope. In particular embodiments, "rate of change of abundance" can refer to a rate of change in abundance of a true labor marker over time, such as during the course of pregnancy. In particular embodiments, when a marker is measured at a first time-point (T1) and a second time-point (T2), "rate of change of abundance" can be defined as $(Abundance_{T2} - Abundance_{T1})/(GA_{T2} - GA_{T1})$, wherein GA refers to gestational age and can be measured in weeks. In particular embodiments, the rate of change of abundance of a true labor marker is significantly changed in an individual experiencing true labor, as compared to the rate of change of abundance of said true labor marker in an individual who is not experiencing true labor.

In particular embodiments, a "significantly changed slope" can refer to an increase or decrease of more than 20%, more than 30%, more than 40%, more than 50%, more than 60%, more than 70%, more than 80%, more than 90%, more than 100%, more than 150%, or more than 200% compared to a reference slope. In particular embodiments, "significantly changed slope" can be evaluated independently against a reference slope without consideration of earlier comparisons in the same subject. In particular embodiments, "significantly changed slope" can be evaluated against a reference slope that is calculated based on measured obtained earlier from the same subject.

In particular embodiments, a "reference slope" can refer to a slope calculated from "normal", "control", "non-labor", "pre-labor" or "false labor" levels or values. In particular embodiments, a "reference slope" can be calculated using reference levels obtained from (i) a non-pregnant subject; or (ii) a pregnant subject not in labor. In particular embodiments, the subject whose samples are used to calculate a reference slope can be a distinct individual from the subject who is being tested for true labor. In particular embodiments, the subject whose samples are used to calculate the "reference slope" can be the same subject who is being tested for true labor. When samples from the same subject are used for the reference slope, the reference slope samples can be collected at earlier time-points, either before pregnancy or at earlier time-points during pregnancy.

In particular embodiments, change of abundance or rate of change of abundance can be used in a model to calculate a true labor score. In particular embodiments, the true labor score is calculated using a linear discriminant analysis (LDA) model. LDA is a method that can be used to classify data points into decision zones based on a linear combination of features. In particular embodiments, the decision zones can include true labor and false labor. In particular embodiments, LDA can use a linear combination of the measurements of true labor markers to distinguish between decision zones, including true labor and false labor. In particular embodiments, LDA can be used to calculate true labor score (1), wherein rate of change of abundance (or slope) of true labor markers can be used as input values in the model (see FIG. 13). In particular embodiments, LDA can be used to calculate true labor score (2), wherein change of abundance of true labor markers can be used as input values in the model. In particular embodiments, a true labor score is an output value of the LDA. In particular embodiments, a true labor score can be a numerical value, wherein a score above a particular threshold value indicates true labor and a score below a particular threshold value indicates false labor.

"Interpretation functions," as used herein, means the transformation of a set of observed data into a meaningful determination of particular interest; e.g., an interpretation function may be a predictive model that is created by utilizing one or more statistical algorithms to transform a dataset of observed biomarker data into a meaningful determination of likelihood of true labor in a subject.

Systems disclosed herein include kits to assay the biomarkers disclosed herein. Also disclosed herein are kits including one or more antibodies, binding proteins, primers and/or probes to assay the biomarkers described herein. In particular embodiments, the kits may include one or more containers containing one or more antibodies, binding proteins, primers and/or probes to be used to assay the biomarkers described herein. Associated with such container(s) can be a safety notice. In particular embodiments, kits disclosed herein include antibodies, binding proteins, primers, probes, and amplification and detection reagents, detectable labels or subsets thereof.

In particular embodiments, the kits may include instructions for using the kit in the methods disclosed herein. In particular embodiments, the kit may include instructions regarding preparation of the antibodies, binding proteins, primers and/or probes, use of the antibodies, binding proteins, primers and/or probes, proper disposal of the related waste, interpretation of results, and the like. The instructions can be in the form of printed instructions provided inside a carton containing the kit. The instructions can also be printed on the carton and/or on other portions of the kit. Instructions may be in the form of a sheet, pamphlet, brochure, CD-Rom, or computer-readable device, or can provide directions to instructions at a remote location, such as a website. The instructions may be in English and/or in any national or regional language.

In particular embodiments, the kits described herein include some or all of the necessary supplies needed to use the kit, thereby eliminating the need to locate and gather such supplies. The supplies can include pipettes, pipette tips, buffers, reagents, plates, films, tubes, thermocyclers, tube racks, gloves, sterilizing liquids, and the like.

The Example below is included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

Example 1. The rate of change of specific maternal plasma protein abundance predicts spontaneous labor at term. The mechanism of parturition is complex and still not completely understood. Labor per se is a retrospective diagnosis. The objective of this Example was to determine whether changes in maternal plasma protein concentrations can predict and/or define labor at term.

A longitudinal study was conducted including 2 separate datasets: 1) normal term pregnancy with (n=20) and without spontaneous labor (n=20); and 2) normal term pregnancy without spontaneous labor (n=50). Longitudinal maternal plasma samples were collected between 8-42 weeks. The gestational age at the last time point ranged between 37-40 weeks (median 39) while the second-to-last point ranged from 33-36 weeks (median: 35.5) for both groups (with and without spontaneous labor). Each dataset was obtained in a different experimental batch using Aptamer proteomics assays. The rate of change (slope) in protein abundance between the last two samples available for each patient was computed. Linear discriminant analysis prediction models were built using up to four best predictors based either on the protein abundance at the last time point or the slope across the last two time points. On the first dataset, a repeated (100 iterations) hold-out procedure was used to build models on 75% of the subjects and test the models on to the remaining 25% of the subjects to compute sensitivity, specificity and area under ROC curves.

The final models (one based on slopes and one on the abundance at last point) were trained with the same methodology on 100% of the patient data and then applied to the second dataset (women without spontaneous labor) to obtain a second independent estimate of specificity of these models.

When the slope of protein abundance between the last two time points in each pregnancy was used, the cross-validated performance of four proteins had a sensitivity of 60% and specificity of 94% (AUC=0.85). The performance of the final model had a sensitivity of 75% and specificity at 100% (AUC=0.94) as assessed by leave-one-out cross-validation based on a fixed set of four proteins that included B7-H2, SORC2, TF, and C1-Esterase Inhibitor. B7-H2 contributed most to the predictive power and had an AUC=0.88. When applied to a second dataset obtained in a different experimental batch, the model based on the slopes of four proteins confirmed its high specificity (90%), unlike the model built using the protein abundance at the last time point only (specificity of 78%).

This Example shows that determining the rate of change in abundance of four proteins after 33 weeks of gestation is predictive of the onset of labor at term. The model has a high specificity which could be used to decrease the index of suspicion of labor. The top predictor among these proteins was B7-H2 which is a ligand for the T-cell-specific cell surface receptor ICOS.

Materials and Methods. Study design. A longitudinal study was conducted by searching the clinical database and Bank of Biologic samples of Wayne State University, the Detroit Medical Center and the Perinatology Research Branch (NICHD/NIH). The inclusion criteria were: 1) singleton gestation; 2) gestational age at delivery 37 weeks; and 3) the absence of fetal malformations. Two separate datasets were included in this study: 1) normal term pregnancy with (n=20) and without spontaneous labor (n=20) ("data set 1"); and 2) normal term pregnancy without spontaneous labor (n=50) ("data set 2"). The majority of patients at term without spontaneous labor had elective cesarean delivery (i.e. due to prior cesarean delivery, malpresentation or non-reassuring fetal status).

Plasma samples were obtained at the time of each prenatal visit, scheduled at four-week intervals from the first or early second trimester until delivery. Each patient had at least three samples collected at any of the following gestational age intervals (8-<16 weeks, 16-<24 weeks, 24-<28 weeks, 28-<32 weeks, 32-<37 weeks and ≥37 weeks) and a maximum of six samples were collected per patient.

All patients provided a written informed consent for their participation in the study. The use of biological specimens as well as clinical and ultrasound data for research purposes were approved by the Wayne State University and Institutional Review Boards of NICHD.

Proteomics technique: The SOMAmer® (Slow Off-rate Modified Aptamers, SomaLogic Inc, Boulder, Colo.) binding reagents that allow the measurement of over 1,125 proteins in maternal plasma samples were used (Gold et al., PloS one 2010; 5(12):e15004; Davies et al., PNAS 2012; 109(49):19971-6; and SomaLogic.SOMAmer® Technical Notes. Proteomics profiling was performed by SomaLogic Inc who commercializes the technology and all needed reagents. The patient serum sample was diluted and then incubated with the respective SOMAmer® mixes pre-immobilized onto streptavidin (SA)-coated beads. The beads were washed to remove all non-specifically associated proteins and other matrix constituents. Proteins that remained specifically bound to their cognate SOMAmer® reagents were tagged using an NHS-biotin reagent. After the labeling reaction, the beads were exposed to an anionic competitor solution that prevents non-specific interactions from reforming after they are disrupted. Essentially pure cognate-SOMAmer® complexes and unbound (free) SOMAmer® reagents are released from the SA beads using ultraviolet light that cleaves the photo-cleavable linker. The photocleavage eluate, which contains all SOMAmer® reagents (some bound to a biotin-labeled protein and some free), was separated from the beads and then incubated with a second streptavidin-coated bead that binds the biotin-labeled proteins and the biotin-labeled protein-SOMAmer® complexes. The free SOMAmer® reagents were then removed during subsequent washing steps. In the final elution step, proteinbound SOMAmer® reagents were released from their cognate proteins using denaturing conditions. These SOMAmer® reagents were then quantified by hybridization to custom DNA microarrays. The Cyanine-3 signal from the SOMAmer® reagent was detected on microarrays.

Clinical definition: Patients with a normal pregnancy were those who delivered healthy term (≥37 weeks) infants whose birthweight was appropriate for the gestational age (AGA) (10th-90th percentile). Before the current disclosure, spontaneous labor at term was diagnosed in the presence of spontaneous regular uterine contractions occurring at a minimum frequency of two every 10 minutes with cervical changes that required hospital admission.

Statistical analysis: Demographics data analysis: The Kolmogorov-Smirnov test was used to assess whether the observations met a normal distribution. Comparisons of continuous data were analyzed using the Kruskal-Wallis and Mann-Whitney U tests. Statistical analysis was performed with SPSS software (version 19; IBM Corporation, Armonk, N.Y.) and the R statistical software. A p value of <0.05 was considered statistically significant.

Development of proteomics based classifiers: Since changes in protein abundance indicative of the onset of labor were expected to be found close to the time of labor, the analysis of the longitudinal dataset 1 was focused on the last two measurement points during pregnancy. Therefore, protein profiles at the time of labor (last sample) and the most recent sample before the onset of labor (second to last sample) were included in the analysis. The rate of the change (slope) in protein abundance between the last two samples of each patient was calculated. LDA prediction models were built based either on the protein abundance at the last time point or the rate of change across the last two time points. To allow both prediction model development and estimation of prediction performance on dataset 1 (TIL n=20; TNL n=20), a repeated (100 iterations) hold-out cross-validation procedure was used. At each iteration data from 75% of the subjects selected randomly was used to develop a prediction model which was then tested on the remaining 25% of the subjects to compute sensitivity, specificity and area under receiver operator characteristics (ROC) curves (AUC). These performance metrics were then averaged over the 100 iterations and reported.

Development of the LDA prediction models on the training data at each iteration was based on a procedure similar to that described in Tarca et al., Systems Biomedicine 2013; 1(4) that has shown to perform well in multiple international systems biology competitions in which high-dimensional data was used to develop prediction models (Tarca et al., Bioinformatics 2013; 29(22):2892-9; Dayarian et al., Bioinformatics 2015; 31(4):462-70). Briefly, given a training dataset (1,125 proteins for 15 TIL and 15 TNL patients) the proteins were ranked based on p-values from a t-test comparing the data (protein measurement at last point or slope over last two time points) between groups. The top four proteins with p<0.05 and (eventually) difference in means greater than a minimum cut-off were retained. The cut-off used amounts to 1.5 fold in average protein abundance between groups for the last point analysis and its equivalent for the slope based analysis. Increasing combinations of up to four proteins were used as predictors in an LDA model, and the optimal combination size was determined by maximizing the AUC statistic of the model evaluated by leaveone-out cross-validation on the training data.

The final models (one based on slopes and one on the abundance at last point) were trained with the same methodology on 100% of the dataset 1 and then applied to the dataset 2 (women without spontaneous labor) to obtain a second independent estimate of specificity of these models.

Results. Clinical characteristics. The demographic and clinical characteristics of the study population are shown in FIG. 8. There were no significant differences in maternal age, pre-pregnancy body mass index (BMI), race and percentage of nulliparity between patients with and without labor in Dataset 1. Patients with term delivery and spontaneous labor had significantly higher gestational age at delivery, birthweight and cesarean delivery rate than those without spontaneous labor (p<0.05 for all) (FIG. 8). A total of 50 patients with normal pregnancy and no spontaneous labor were included in dataset 2. The median (interquartile range) gestational age at delivery and birthweight were 40.0 (39.0-40.8) weeks of gestation and 3,393 (3,101-3,620) grams, respectively. The frequency of cesarean delivery was 70% (35/50) (FIG. 8).

Protein markers for spontaneous labor at term. Prediction performance of protein abundance at last sample: The estimated prediction performance of a multi-marker LDA model was 60% sensitivity at 88% specificity (AUC=0.77) based on 100 iterations hold-out procedure in which 75% of the patients were used for training the model and 25% were used for testing. The final model based on proteins selected on the entire dataset 1 included TF, Ran, Phosphoglycerate mutase 1, and Inosine-5'-monophosphate dehydrogenase 1 (IMDH1). The longitudinal profiles of these four proteins demonstrating the differences between TIL and TNL groups at the last time point are shown in FIG. 9A and FIGS. 10C-10E. Of note, the four proteins selected in the prediction model are the only ones out of the 1,125 measured that would be deemed significant in a differential abundance analysis at false discovery rate of 5% (based on two-tailed t-tests) and at least 1.5 fold change in protein abundance between groups (at the last sample).

The leave-one-out cross-validated performance of these four proteins had a 70% sensitivity and 100% specificity (AUC=0.95). When the prediction model was applied on the second dataset containing data from 50 TNL patients and obtained in another experimental batch, the prediction model based on absolute protein abundance had a specificity of 78% (sensitivity could not be determined since no TIL cases were available in dataset 2).

Prediction performance of protein abundance rate of change with gestation: When the rate of change in protein abundance between last and second to last sample was used for analysis, the estimated prediction performance of a multi-marker LDA model was 60% sensitivity at 94% specificity (AUC=0.85) based on 100 iterations hold-out procedure. The final model based on proteins selected on the entire dataset 1 included B7-H2, SORC2, TF, and C1-Esterase Inhibitor. The longitudinal profiles of these proteins demonstrating different rates of change from second to last to the last sample between TIL and TNL patients are shown in FIGS. 9A and 9B and FIGS. 10A and 10B. Of note, the top three of the four proteins selected in the prediction model (B7-H2, SORC2, and TF) would be deemed significant in a differential abundance analysis at false discovery rate of 5% (based on two-tailed t-tests) and an effect size equivalent to at least 1.5 fold change at the last point and same average abundance at the second to last point.

The leave-one-out cross-validated performance of these four proteins had a 75% sensitivity and 100% specificity (AUC=0.94). When the prediction model was applied on the second dataset containing data from 50 TNL patients and obtained in another experimental batch, the prediction model based on rate of change in protein abundance had a specificity of 90% (sensitivity could not be determined since no TIL cases were available in dataset 2). Of note, the largest contribution to the prediction performance of the set of four proteins is attributed to B7-H2 (FIG. 11). The calculation and distributions of the slopes for B7-H2 in the TNL and TIL patients are shown in FIG. 12.

Figure 13:
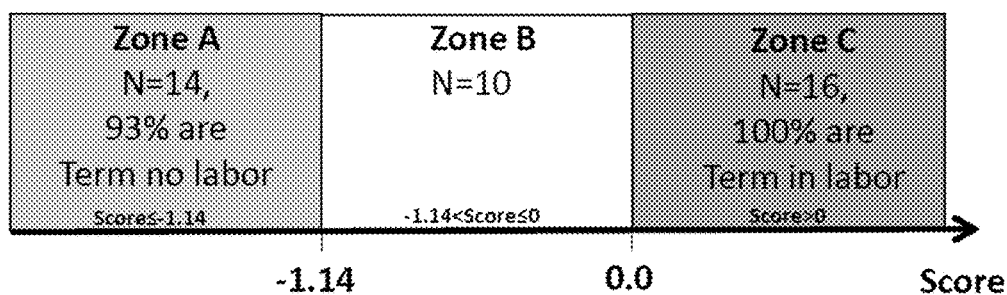
FIG. 13. Decision zones based on the four-protein slope model. The slopes of the proteins in the gestational age interval 33 to 40 weeks are first calculated as described and illustrated in FIG. 12. A risk score is computed from the slopes of the four proteins as: Score=4.422*S(B7–H2)−5.981*S(SORC2)−0.538*S(TF)−0.033*S(C1-Esterase Inhibitor)+1.314, where S stands for the slope of protein abundance estimated in the 33 to 40 weeks of gestation interval. Zone A: Score≤−1.14; Zone B: −1.14<Score≤0; Zone C: Score>0.

Using two cut-offs on the estimated probability of each patient to have spontaneous labor ($P_{labor}$) as provided by the LDA slope model, three prediction zones were identified: Zone A) $P_{labor}$<0.04, 35% (14/40) of patients; 93% (13/14) of these did not have spontaneous labor; Zone B) 0.04≤$P_{labor}$<0.47, 25% (10/40) of patients; and Zone C) $P_{labor}$≥0.47, 40% (16/40) of patients; all of them (16/16) had spontaneous labor (FIG. 13).

Discussion Principal findings of the Example: 1) The cross-validated performance of a classifier using the rate of change in protein abundance of up to four proteins (out of 1,125 proteins available in the SomaLogic platform), had a sensitivity of 60% and a specificity of 94% (AUC=0.85) for diagnosis of term labor; 2) the performance of the final model had a sensitivity of 75% and specificity of 100% (AUC=0.94) as assessed by leave-one-out cross-validation based on a fixed set of four proteins that included B7-H2, SORC2, TF, and C1-Esterase Inhibitor; 3) B7-H2 contributed most to the predictive power of the rate of change in protein abundance between the last two measurement points, as it had an AUC=0.88 alone; and 4) when applied to a second dataset obtained in a different experimental batch, the model based on the slopes of four proteins confirmed its high specificity (90%), unlike the model built using the protein abundance at the last time point only (specificity of 78%).

The finding of this longitudinal Example that four proteins in maternal blood (determined at 4 weeks before labor and at the time of labor) can predict true labor with a high specificity is novel. These four proteins have biological plausibility associated with the process of parturition. Interestingly, the change in protein abundance of B7-H2 contributed the most for the prediction of labor. This protein participates in the regulation of T-effector-cell function, Ig isotype class switching and cytokine production (IFN-γ, IL-4 and IL-10). Its effect is mainly in the decidua and not in the maternal circulation suggestive of activation of the inflammatory processes leading to the onset of parturition. Changes in inflammatory system were reported in all components of the common pathway of parturition. Indeed, labor is characterized by inflammatory processes in the cervix, myometrium choriodecidua and amniotic fluid.

An additional protein that changed substantially prior to term birth is tissue factor, the natural activator of the coagulation cascade. Changes in the maternal coagulation system have been reported in term and preterm labor (e.g. Keren-Politansky et al., Thrombosis research 2014; 133(4): 585-9). The activation and the changes in the coagulation cascade during parturition results from two elements, the first is the impact of inflammation that activates the coagulation cascade and the second is decidual activation that releases tissue factor. The third protein that is changing is the Sortilin-related VPS10 domain containing receptor 2 (SorCS2). This protein is one a family member of vascular protein sorting 10 and is involved in protein transcript, signal transduction, neurogenesis, and functional maintenance of the nervous system. The function of SorCS2 remains to be elucidated. The last protein, plasma protease C1 inhibitor, is the inhibitor of the classical activation of the complement system. Its decrease prior to labor may enable the activation of the complement as part of the inflammatory response associated with parturition. Collectively, this set of proteins that change in abundance with the onset of labor represent major biological pathways that participate in the process of human parturition.

The high specificity of the four proteins identified from the analysis herein can be used to decrease the index of suspicion for true labor. This has important clinical implications since in the presence of a negative result, patients are unlikely to deliver. Therefore, hospital admission and interventions such as the administration of analgesia and uterotonic agents will not be necessary. Also, compelling evidence shows that the false diagnosis of true labor increases the rate of induction and augmentation of labor, amniotomy, operative delivery as well as cesarean delivery.

Of the four proteins selected as predictive of spontaneous labor based on their abundance at last sample, TF and PGAM1 exhibited consistent lower levels in the labor group than in controls only at last sample, but not earlier (FIG. 9A and FIG. 10D). In contrast, Ran and IMDH1 appear to have higher levels even earlier in pregnancy (FIGS. 10O and 10E), yet the within group variability in the data is high. The use of within patient rate of change in protein abundance over the last two time points (slope) enabled the discovery VPS10 domain-containing receptor SorCS2 (SORC2) whose absolute levels do not distinguish between groups at any time point yet a sharp decrease in its abundance is specific to patients in labor. Moreover, the slope based analysis reduces the patient to patient variability and increase discrimination for proteins such as B7-H2, TF, and C1-Esterase Inhibitor which exhibit differences in mean abundance at the last sample.

This variability is contributed by unknown patient characteristics that affect the absolute level of these proteins, as well by slight differences in gestational age at last sample. The reduction in this unwanted variability is possible as each patient becomes its own control and is akin to the use of a fetal growth chart as opposed to a fetal size chart for detection of growth restriction.

This Example demonstrates that the measurement of proteins in maternal blood identifies patients experiencing true labor. In particular embodiments, these protein can be used in combination with clinical signs and symptoms, along with other labor indicators, such as cervical length to diagnose a patient as experiencing true or false labor. The strengths of this Example include longitudinal collection of samples, the use of novel proteomics technique which can measure more than one-thousand proteins simultaneously, and the robust statistical model development and evaluation strategy that relies on cross-validation.

As will be understood by one of ordinary skill in the art, each embodiment disclosed herein can comprise, consist essentially of, or consist of its particular stated element, step, ingredient or component. Thus, the terms "include" or "including" should be interpreted to recite: "comprise, consist of, or consist essentially of." As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. As used herein, a material effect would cause a statistically significant reduction in the specificity of the assessment of the presence of true labor.

Unless otherwise indicated, all numbers used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to publications, patents and/or patent applications (collectively "references") throughout this specification. Each of the cited references is individually incorporated herein by reference for their particular cited teachings.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method, comprising:
   obtaining a sample from a pregnant female experiencing symptoms associated with false labor and true labor; and
   measuring in the sample for abundance of:
   (i) tissue factor (TF), ICOS Ligand (B7-H2), VPS10 Domain Containing Receptor SorCS2 (SORC2), and Plasma Protease C1 Inhibitor (C1-Esterase Inhibitor); or
   (ii) TF, Ras-related Nuclear protein (Ran), Inosine-5'-monophosphate dehydrogenase (IMDH1), and Phosphoglycerate mutase 1 (PGAM1).

2. The method of claim 1, comprising:
   measuring TF, B7-H2, SORC2, C1-Esterase Inhibitor.

3. The method of claim 1(i) or claim 2, further comprising calculating a rate of change of abundance of TF, B7-H2, SORC2, and C1-Esterase Inhibitor between two samples obtained from the same pregnant female at two different times, and
   using the calculated rate of change of abundance to identify whether the pregnant female is in true labor or false labor.

4. The method of claim 3, wherein the calculating of the rate of change of abundance of TF, B7-H2, SORC2, and C1-Esterase Inhibitor is the formula:
   $(Abundance_{T2} - Abundance_{T1})/(GA_{T2} - GA_{T1})$, wherein GA refers to gestational age and can be measured in weeks, wherein $T_1$ refers to a first time-point and a $T_2$ refers to a second, later time-point.

5. The method of claim 4, wherein:
   (a) $GA_{T2}$ and $GA_{T1}$ are between 33 and 40 weeks; and/or
   (b) the rate of change of abundance is used to calculate a true labor score (1), according to the formula:

true labor score$(1) = 4.4*S_{(B7-H2)} - 5.9*S_{(Sorc2)} - 0.5*S_{(TF)} - 0.03*S_{(C1-Esterase\ Inhibitor)} + 1.1$, or true labor score$(1) = 4.422*S_{(B7-H2)} - 5.981*S_{(Sorc2)} - 0.538*S_{(TF)} - 0.033*S_{(C1-Esterase\ Inhibitor)} + 1.134$, wherein S refers to the rate of change of abundance.

6. The method of claim 1, wherein:
   the sample obtained from a pregnant female is collected between 33 and 40 weeks of the female's pregnancy; and/or
   the sample is obtained when the pregnant female is experiencing symptoms associated with false labor and true labor; and/or
   the symptoms are contractions; and/or
   the samples are plasma or serum samples.

7. The method of claim 1(ii) or 2, further comprising calculating changes in abundance (CA) of TF, Ran, IMDH1, and PGAM1 as compared to a value derived from a reference population that has not experienced true labor; and
   using the calculated change in abundance to identify whether the pregnant female is in true labor or false labor.

8. The method of claim 7, comprising:
   calculating a true labor score(2), wherein $CA_{TF}$, $CA_{Ran}$, $CA_{IMDH1}$, and $CA_{PGAM1}$ are used in a Linear Discriminant Analysis Model; and/or
   analysis of true labor score(2);
   wherein the true labor score(2) comprises two threshold values, X and Y,
   wherein a true labor score(2)≤X denotes that the pregnant female is in false labor, and a true labor score(2)>Y denotes that the pregnant female is in true labor; and
   using the calculated true labor score(2) to identify whether the pregnant female is in true labor or false labor.

9. A method, comprising:
   obtaining a sample from a pregnant female experiencing symptoms associated with false labor and true labor; and
   measuring in the sample a level or an amount of each of:
   (i) tissue factor (TF), ICOS Ligand (B7-H2), VPS10 Domain Containing Receptor SorCS2 (SORC2), and Plasma Protease C1 Inhibitor (C1-Esterase Inhibitor); or
   (ii) TF, Ras-related Nuclear protein (Ran), Inosine-5'-monophosphate dehydrogenase (IMDH1), and Phosphoglycerate mutase 1 (PGAM1).

10. The method of claim 9, comprising measuring the level or amount of each of TF, B7-H2, SORC2, C1-Esterase Inhibitor Ran, IMDH1, and PGAM1.

11. The method of claim 9(i) or claim 10, further comprising calculating a rate of change of level or amount of TF, B7-H2, SORC2, and C1-Esterase Inhibitor between two samples obtained from the same pregnant female at two different times, and
    using the calculated rate of change of level or amount to identify whether the pregnant female is in true labor or false labor.

12. The method of claim 11, wherein the calculating of the rate of change of level or amount of TF, B7-H2, SORC2, and C1-Esterase Inhibitor is the formula:
    $(AbundanceT2 - Abundance_{T1})/(GAT2 - GA_{T1})$, wherein GA refers to gestational age and can be measured in weeks, wherein $T_1$ refers to a first time-point and a $T_2$ refers to a second, later time-point.

13. The method of claim 12, wherein:
    (a) $GA_{T2}$ and $GA_{T1}$ are between 33 and 40 weeks; and/or
    (b) the rate of change of level or amount is used to calculate a true labor score (1), according to the formula:

true labor score$(1) = 4.4*S_{(B7-H2)} - 5.9*S_{(Sorc2)} - 0.5*S_{(TF)} - 0.03*S_{(C1-Esterase\ Inhibitor)} + 1.1$, or true labor score$(1) = 4.422*S_{(B7-H2)} - 5.981*S_{(sorc2)} - 0.538*S_{(TF)} - 0.033*S_{(C1-Esterase\ Inhibitor)} + 1.134$, wherein S refers to the rate of change of level or amount.

14. The method of claim 9, wherein:
    the sample obtained from a pregnant female is collected between 33 and 40 weeks of the female's pregnancy; and/or
    the sample is obtained when the pregnant female is experiencing symptoms associated with false labor and true labor; and/or
    the symptoms are contractions; and/or
    the samples are plasma or serum samples.

15. The method of claim 9(ii) or 10, further comprising calculating changes in level or amount (CA) of TF, Ran, IMDH1, and PGAM1 as compared to a value derived from a reference population that has not experienced true labor; and using the calculated change in level or amount to identify whether the pregnant female is in true labor or false labor.

16. The method of claim 14, comprising:
calculating a true labor score(2), wherein $CA_{TF}$, $CA_{Ran}$, $CA_{IMDH1}$, and $CA_{PGAM1}$ are used in a Linear Discriminant Analysis Model; and/or
analysis of true labor score(2);
wherein the true labor score(2) comprises two threshold values, X and Y,
wherein a true labor score(2)≤X denotes that the pregnant female is in false labor, and a true labor score(2)>Y denotes that the pregnant female is in true labor; and
using the calculated true labor score(2) to identify whether the pregnant female is in true labor or false labor.

17. A method, comprising:
obtaining a sample from a pregnant female experiencing symptoms associated with false labor and true labor; and
measuring in the sample abundance of tissue factor (TF) in combination with
(i) ICOS Ligand (B7-H2) and/or VPS10 Domain Containing Receptor SorCS2 (SORC2); or
(ii) Ras-related Nuclear protein (Ran), Inosine-5'-monophosphate dehydrogenase (IMDH1), and/or Phosphoglycerate mutase 1 (PGAM1).

18. The method of claim 17, comprising:
(a) assessing TF in combination with B7-H2, SORC2, and C1-Esterase Inhibitor; or
(b) assessing TF in combination with Ran, IMDH1, and PGAM1; or
(c) both (a) and (b).

19. The method of claim 17, wherein:
the sample obtained from a pregnant female is collected between 33 and 40 weeks of the female's pregnancy; and/or
the sample is obtained when the pregnant female is experiencing symptoms associated with false labor and true labor; and/or
the symptoms are contractions; and/or
the samples are plasma or serum samples.

* * * * *

SEQUENCE LISTING

```
<160> NUMBER OF SEQ ID NOS: 7

<210> SEQ ID NO 1
<211> LENGTH: 302
<212> TYPE: PRT
<213> ORGANISM: Homo sapiens

<400> SEQUENCE: 1

Met Arg Leu Gly Ser Pro Gly Leu Leu Phe Leu Leu Phe Ser Ser Leu
1               5                   10                  15

Arg Ala Asp Thr Gln Glu Lys Glu Val Arg Ala Met Val Gly Ser Asp
                20                  25                  30

Val Glu Leu Ser Cys Ala Cys Pro Glu Gly Ser Arg Phe Asp Leu Asn
            35                  40                  45

Asp Val Tyr Val Tyr Trp Gln Thr Ser Glu Ser Lys Thr Val Val Thr
        50                  55                  60

Tyr His Ile Pro Gln Asn Ser Ser Leu Glu Asn Val Asp Ser Arg Tyr
65                  70                  75                  80

Arg Asn Arg Ala Leu Met Ser Pro Ala Gly Met Leu Arg Gly Asp Phe
                85                  90                  95

Ser Leu Arg Leu Phe Asn Val Thr Pro Gln Asp Glu Gln Lys Phe His
            100                 105                 110

Cys Leu Val Leu Ser Gln Ser Leu Gly Phe Gln Glu Val Leu Ser Val
            115                 120                 125

Glu Val Thr Leu His Val Ala Ala Asn Phe Ser Val Pro Val Val Ser
        130                 135                 140

Ala Pro His Ser Pro Ser Gln Asp Glu Leu Thr Phe Thr Cys Thr Ser
145                 150                 155                 160

Ile Asn Gly Tyr Pro Arg Pro Asn Val Tyr Trp Ile Asn Lys Thr Asp
                165                 170                 175

Asn Ser Leu Leu Asp Gln Ala Leu Gln Asn Asp Thr Val Phe Leu Asn
            180                 185                 190

Met Arg Gly Leu Tyr Asp Val Val Ser Val Leu Arg Ile Ala Arg Thr
        195                 200                 205

Pro Ser Val Asn Ile Gly Cys Cys Ile Glu Asn Val Leu Leu Gln Gln
    210                 215                 220

Asn Leu Thr Val Gly Ser Gln Thr Gly Asn Asp Ile Gly Glu Arg Asp
225                 230                 235                 240

Lys Ile Thr Glu Asn Pro Val Ser Thr Gly Glu Lys Asn Ala Ala Thr
                245                 250                 255

Trp Ser Ile Leu Ala Val Leu Cys Leu Leu Val Val Val Ala Val Ala
            260                 265                 270
```

Ile Gly Trp Val Cys Arg Asp Arg Cys Leu Gln His Ser Tyr Ala Gly
        275                 280                 285

Ala Trp Ala Val Ser Pro Glu Thr Glu Leu Thr Gly His Val
    290                 295                 300

<210> SEQ ID NO 2
<211> LENGTH: 1159
<212> TYPE: PRT
<213> ORGANISM: Homo Sapiens

<400> SEQUENCE: 2

Met Ala His Arg Gly Pro Ser Arg Ala Ser Lys Gly Pro Gly Pro Thr
1               5                   10                  15

Ala Arg Ala Pro Ser Pro Gly Ala Pro Pro Pro Arg Ser Pro Arg
            20                  25                  30

Ser Arg Pro Leu Leu Leu Leu Leu Leu Leu Gly Ala Cys Gly Ala
            35                  40                  45

Ala Gly Arg Ser Pro Glu Pro Gly Arg Leu Gly Pro His Ala Gln Leu
    50                  55                  60

Thr Arg Val Pro Arg Ser Pro Pro Ala Gly Arg Ala Glu Pro Gly Gly
65                  70                  75                  80

Gly Glu Asp Arg Gln Ala Arg Gly Thr Glu Pro Gly Ala Pro Gly Pro
                85                  90                  95

Ser Pro Gly Pro Ala Pro Pro Gly Glu Asp Gly Ala Pro Ala Ala
            100                 105                 110

Gly Tyr Arg Arg Trp Glu Arg Ala Ala Pro Leu Ala Gly Val Ala Ser
            115                 120                 125

Arg Ala Gln Val Ser Leu Ile Ser Thr Ser Phe Val Leu Lys Gly Asp
    130                 135                 140

Ala Thr His Asn Gln Ala Met Val His Trp Thr Gly Glu Asn Ser Ser
145                 150                 155                 160

Val Ile Leu Ile Leu Thr Lys Tyr Tyr His Ala Asp Met Gly Lys Val
                165                 170                 175

Leu Glu Ser Ser Leu Trp Arg Ser Ser Asp Phe Gly Thr Ser Tyr Thr
            180                 185                 190

Lys Leu Thr Leu Gln Pro Gly Val Thr Thr Val Ile Asp Asn Phe Tyr
            195                 200                 205

Ile Cys Pro Thr Asn Lys Arg Lys Val Ile Leu Val Ser Ser Ser Leu
    210                 215                 220

Ser Asp Arg Asp Gln Ser Leu Phe Leu Ser Ala Asp Glu Gly Ala Thr
225                 230                 235                 240

Phe Gln Lys Gln Pro Ile Pro Phe Phe Val Glu Thr Leu Ile Phe His
                245                 250                 255

Pro Lys Glu Glu Asp Lys Val Leu Ala Tyr Thr Lys Glu Ser Lys Leu
            260                 265                 270

Tyr Val Ser Ser Asp Leu Gly Lys Lys Trp Thr Leu Leu Gln Glu Arg
            275                 280                 285

Val Thr Lys Asp His Val Phe Trp Ser Val Ser Gly Val Asp Ala Asp
    290                 295                 300

Pro Asp Leu Val His Val Glu Ala Gln Asp Leu Gly Gly Asp Phe Arg
305                 310                 315                 320

Tyr Val Thr Cys Ala Ile His Asn Cys Ser Glu Lys Met Leu Thr Ala
                325                 330                 335

Pro Phe Ala Gly Pro Ile Asp His Gly Ser Leu Thr Val Gln Asp Asp

```
            340                 345                 350
Tyr Ile Phe Phe Lys Ala Thr Ser Ala Asn Gln Thr Lys Tyr Tyr Val
            355                 360                 365

Ser Tyr Arg Arg Asn Glu Phe Val Leu Met Lys Leu Pro Lys Tyr Ala
370                 375                 380

Leu Pro Lys Asp Leu Gln Ile Ile Ser Thr Asp Glu Ser Gln Val Phe
385                 390                 395                 400

Val Ala Val Gln Glu Trp Tyr Gln Met Asp Thr Tyr Asn Leu Tyr Gln
                    405                 410                 415

Ser Asp Pro Arg Gly Val Arg Tyr Ala Leu Val Leu Gln Asp Val Arg
                420                 425                 430

Ser Ser Arg Gln Ala Glu Glu Ser Val Leu Ile Asp Ile Leu Glu Val
                435                 440                 445

Arg Gly Val Lys Gly Val Phe Leu Ala Asn Gln Lys Ile Asp Gly Lys
                450                 455                 460

Val Met Thr Leu Ile Thr Tyr Asn Lys Gly Arg Asp Trp Asp Tyr Leu
465                 470                 475                 480

Arg Pro Pro Ser Met Asp Met Asn Gly Lys Pro Thr Asn Cys Lys Pro
                485                 490                 495

Pro Asp Cys His Leu His Leu His Leu Arg Trp Ala Asp Asn Pro Tyr
                500                 505                 510

Val Ser Gly Thr Val His Thr Lys Asp Thr Ala Pro Gly Leu Ile Met
                515                 520                 525

Gly Ala Gly Asn Leu Gly Ser Gln Leu Val Glu Tyr Lys Glu Glu Met
                530                 535                 540

Tyr Ile Thr Ser Asp Cys Gly His Thr Trp Arg Gln Val Phe Glu Glu
545                 550                 555                 560

Glu His His Ile Leu Tyr Leu Asp His Gly Gly Val Ile Val Ala Ile
                565                 570                 575

Lys Asp Thr Ser Ile Pro Leu Lys Ile Leu Lys Phe Ser Val Asp Glu
                580                 585                 590

Gly Leu Thr Trp Ser Thr His Asn Phe Thr Ser Thr Ser Val Phe Val
                595                 600                 605

Asp Gly Leu Leu Ser Glu Pro Gly Asp Glu Thr Leu Val Met Thr Val
                610                 615                 620

Phe Gly His Ile Ser Phe Arg Ser Asp Trp Glu Leu Val Lys Val Asp
625                 630                 635                 640

Phe Arg Pro Ser Phe Ser Arg Gln Cys Gly Glu Glu Asp Tyr Ser Ser
                645                 650                 655

Trp Glu Leu Ser Asn Leu Gln Gly Asp Arg Cys Ile Met Gly Gln Gln
                660                 665                 670

Arg Ser Phe Arg Lys Arg Lys Ser Thr Ser Trp Cys Ile Lys Gly Arg
                675                 680                 685

Ser Phe Thr Ser Ala Leu Thr Ser Arg Val Cys Glu Cys Arg Asp Ser
                690                 695                 700

Asp Phe Leu Cys Asp Tyr Gly Phe Glu Arg Ser Ser Ser Ser Glu Ser
705                 710                 715                 720

Ser Thr Asn Lys Cys Ser Ala Asn Phe Trp Phe Asn Pro Leu Ser Pro
                725                 730                 735

Pro Asp Asp Cys Ala Leu Gly Gln Thr Tyr Thr Ser Ser Leu Gly Tyr
                740                 745                 750

Arg Lys Val Val Ser Asn Val Cys Glu Gly Gly Val Asp Met Gln Gln
                755                 760                 765
```

```
Ser Gln Val Gln Leu Gln Cys Pro Leu Thr Pro Pro Arg Gly Leu Gln
    770                 775                 780

Val Ser Ile Gln Gly Glu Ala Val Ala Val Arg Pro Gly Glu Asp Val
785                 790                 795                 800

Leu Phe Val Val Arg Gln Glu Gln Gly Asp Val Leu Thr Thr Lys Tyr
                    805                 810                 815

Gln Val Asp Leu Gly Asp Gly Phe Lys Ala Met Tyr Val Asn Leu Thr
                820                 825                 830

Leu Thr Gly Glu Pro Ile Arg His Arg Tyr Glu Ser Pro Gly Ile Tyr
            835                 840                 845

Arg Val Ser Val Arg Ala Glu Asn Thr Ala Gly His Asp Glu Ala Val
    850                 855                 860

Leu Phe Val Gln Val Asn Ser Pro Leu Gln Ala Leu Tyr Leu Glu Val
865                 870                 875                 880

Val Pro Val Ile Gly Leu Asn Gln Glu Val Asn Leu Thr Ala Val Leu
                885                 890                 895

Leu Pro Leu Asn Pro Asn Leu Thr Val Phe Tyr Trp Trp Ile Gly His
                900                 905                 910

Ser Leu Gln Pro Leu Leu Ser Leu Asp Asn Ser Val Thr Thr Arg Phe
    915                 920                 925

Ser Asp Thr Gly Asp Val Arg Val Thr Val Gln Ala Ala Cys Gly Asn
    930                 935                 940

Ser Val Leu Gln Asp Ser Arg Val Leu Arg Val Leu Asp Gln Phe Gln
945                 950                 955                 960

Val Met Pro Leu Gln Phe Ser Lys Glu Leu Asp Ala Tyr Asn Pro Asn
                965                 970                 975

Thr Pro Glu Trp Arg Glu Asp Val Gly Leu Val Val Thr Arg Leu Leu
                980                 985                 990

Ser Lys Glu Thr Ser Val Pro Gln Glu Leu Leu Val Thr Val Val Lys
    995                 1000                1005

Pro Gly Leu Pro Thr Leu Ala Asp Leu Tyr Val Leu Leu Pro Pro
    1010            1015                1020

Pro Arg Pro Thr Arg Lys Arg Ser Leu Ser Ser Asp Lys Arg Leu
    1025            1030                1035

Ala Ala Ile Gln Gln Val Leu Asn Ala Gln Lys Ile Ser Phe Leu
    1040            1045                1050

Leu Arg Gly Gly Val Arg Val Leu Val Ala Leu Arg Asp Thr Gly
    1055            1060                1065

Thr Gly Ala Glu Gln Leu Gly Gly Gly Gly Tyr Trp Ala Val
    1070            1075                1080

Val Val Leu Phe Val Ile Gly Leu Phe Ala Ala Gly Ala Phe Ile
    1085            1090                1095

Leu Tyr Lys Phe Lys Arg Lys Arg Pro Gly Arg Thr Val Tyr Ala
    1100            1105                1110

Gln Met His Asn Glu Lys Glu Gln Glu Met Thr Ser Pro Val Ser
    1115            1120                1125

His Ser Glu Asp Val Gln Gly Ala Val Gln Gly Asn His Ser Gly
    1130            1135                1140

Val Val Leu Ser Ile Asn Ser Arg Glu Met His Ser Tyr Leu Val
    1145            1150                1155

Ser
```

```
<210> SEQ ID NO 3
<211> LENGTH: 295
<212> TYPE: PRT
<213> ORGANISM: Homo sapiens

<400> SEQUENCE: 3

Met Glu Thr Pro Ala Trp Pro Arg Val Pro Arg Pro Glu Thr Ala Val
1               5                   10                  15

Ala Arg Thr Leu Leu Leu Gly Trp Val Phe Ala Gln Val Ala Gly Ala
            20                  25                  30

Ser Gly Thr Thr Asn Thr Val Ala Ala Tyr Asn Leu Thr Trp Lys Ser
        35                  40                  45

Thr Asn Phe Lys Thr Ile Leu Glu Trp Glu Pro Lys Pro Val Asn Gln
    50                  55                  60

Val Tyr Thr Val Gln Ile Ser Thr Lys Ser Gly Asp Trp Lys Ser Lys
65                  70                  75                  80

Cys Phe Tyr Thr Thr Asp Thr Glu Cys Asp Leu Thr Asp Glu Ile Val
                85                  90                  95

Lys Asp Val Lys Gln Thr Tyr Leu Ala Arg Val Phe Ser Tyr Pro Ala
            100                 105                 110

Gly Asn Val Glu Ser Thr Gly Ser Ala Gly Glu Pro Leu Tyr Glu Asn
        115                 120                 125

Ser Pro Glu Phe Thr Pro Tyr Leu Glu Thr Asn Leu Gly Gln Pro Thr
    130                 135                 140

Ile Gln Ser Phe Glu Gln Val Gly Thr Lys Val Asn Val Thr Val Glu
145                 150                 155                 160

Asp Glu Arg Thr Leu Val Arg Arg Asn Asn Thr Phe Leu Ser Leu Arg
                165                 170                 175

Asp Val Phe Gly Lys Asp Leu Ile Tyr Thr Leu Tyr Tyr Trp Lys Ser
            180                 185                 190

Ser Ser Ser Gly Lys Lys Thr Ala Lys Thr Asn Thr Asn Glu Phe Leu
        195                 200                 205

Ile Asp Val Asp Lys Gly Glu Asn Tyr Cys Phe Ser Val Gln Ala Val
    210                 215                 220

Ile Pro Ser Arg Thr Val Asn Arg Lys Ser Thr Asp Ser Pro Val Glu
225                 230                 235                 240

Cys Met Gly Gln Glu Lys Gly Glu Phe Arg Glu Ile Phe Tyr Ile Ile
                245                 250                 255

Gly Ala Val Ala Phe Val Val Ile Ile Leu Val Ile Ile Leu Ala Ile
            260                 265                 270

Ser Leu His Lys Cys Arg Lys Ala Gly Val Gly Gln Ser Trp Lys Glu
        275                 280                 285

Asn Ser Pro Leu Asn Val Ser
    290                 295

<210> SEQ ID NO 4
<211> LENGTH: 500
<212> TYPE: PRT
<213> ORGANISM: Homo sapiens

<400> SEQUENCE: 4

Met Ala Ser Arg Leu Thr Leu Leu Thr Leu Leu Leu Leu Leu Leu Ala
1               5                   10                  15

Gly Asp Arg Ala Ser Ser Asn Pro Asn Ala Thr Ser Ser Ser Ser Gln
            20                  25                  30

Asp Pro Glu Ser Leu Gln Asp Arg Gly Glu Gly Lys Val Ala Thr Thr
```

-continued

```
                35                  40                  45
Val Ile Ser Lys Met Leu Phe Val Glu Pro Ile Leu Glu Val Ser Ser
 50                  55                  60
Leu Pro Thr Thr Asn Ser Thr Asn Ser Ala Thr Lys Ile Thr Ala
 65                  70                  75                  80
Asn Thr Thr Asp Glu Pro Thr Thr Gln Pro Thr Thr Glu Pro Thr Thr
                 85                  90                  95
Gln Pro Thr Ile Gln Pro Thr Gln Pro Thr Thr Gln Leu Pro Thr Asp
                100                 105                 110
Ser Pro Thr Gln Pro Thr Thr Gly Ser Phe Cys Pro Gly Pro Val Thr
                115                 120                 125
Leu Cys Ser Asp Leu Glu Ser His Ser Thr Glu Ala Val Leu Gly Asp
130                 135                 140
Ala Leu Val Asp Phe Ser Leu Lys Leu Tyr His Ala Phe Ser Ala Met
145                 150                 155                 160
Lys Lys Val Glu Thr Asn Met Ala Phe Ser Pro Phe Ser Ile Ala Ser
                165                 170                 175
Leu Leu Thr Gln Val Leu Leu Gly Ala Gly Glu Asn Thr Lys Thr Asn
                180                 185                 190
Leu Glu Ser Ile Leu Ser Tyr Pro Lys Asp Phe Thr Cys Val His Gln
                195                 200                 205
Ala Leu Lys Gly Phe Thr Thr Lys Gly Val Thr Ser Val Ser Gln Ile
                210                 215                 220
Phe His Ser Pro Asp Leu Ala Ile Arg Asp Thr Phe Val Asn Ala Ser
225                 230                 235                 240
Arg Thr Leu Tyr Ser Ser Pro Arg Val Leu Ser Asn Asn Ser Asp
                245                 250                 255
Ala Asn Leu Glu Leu Ile Asn Thr Trp Val Ala Lys Asn Thr Asn Asn
                260                 265                 270
Lys Ile Ser Arg Leu Leu Asp Ser Leu Pro Ser Asp Thr Arg Leu Val
                275                 280                 285
Leu Leu Asn Ala Ile Tyr Leu Ser Ala Lys Trp Lys Thr Thr Phe Asp
                290                 295                 300
Pro Arg Lys Thr Arg Met Glu Pro Phe His Phe Lys Asn Ser Val Ile
305                 310                 315                 320
Lys Val Pro Met Met Asn Ser Lys Lys Tyr Pro Val Ala His Phe Ile
                325                 330                 335
Asp Gln Thr Leu Lys Ala Lys Val Gly Gln Leu Gln Leu Ser His Asn
                340                 345                 350
Leu Ser Leu Val Ile Leu Val Pro Gln Asn Leu Lys His Arg Leu Glu
                355                 360                 365
Asp Met Glu Gln Ala Leu Ser Pro Ser Val Phe Lys Ala Ile Met Glu
                370                 375                 380
Lys Leu Glu Met Ser Lys Phe Gln Pro Thr Leu Leu Thr Leu Pro Arg
385                 390                 395                 400
Ile Lys Val Thr Thr Ser Gln Asp Met Leu Ser Ile Met Glu Lys Leu
                405                 410                 415
Glu Phe Phe Asp Phe Ser Tyr Asp Leu Asn Leu Cys Gly Leu Thr Glu
                420                 425                 430
Asp Pro Asp Leu Gln Val Ser Ala Met Gln His Gln Thr Val Leu Glu
                435                 440                 445
Leu Thr Glu Thr Gly Val Glu Ala Ala Ala Ala Ser Ala Ile Ser Val
450                 455                 460
```

Ala Arg Thr Leu Leu Val Phe Glu Val Gln Gln Pro Phe Leu Phe Val
465                 470                 475                 480

Leu Trp Asp Gln Gln His Lys Phe Pro Val Phe Met Gly Arg Val Tyr
            485                 490                 495

Asp Pro Arg Ala
            500

<210> SEQ ID NO 5
<211> LENGTH: 216
<212> TYPE: PRT
<213> ORGANISM: Homo sapiens

<400> SEQUENCE: 5

Met Ala Ala Gln Gly Glu Pro Gln Val Gln Phe Lys Leu Val Leu Val
1               5                   10                  15

Gly Asp Gly Gly Thr Gly Lys Thr Thr Phe Val Lys Arg His Leu Thr
            20                  25                  30

Gly Glu Phe Glu Lys Lys Tyr Val Ala Thr Leu Gly Val Glu Val His
        35                  40                  45

Pro Leu Val Phe His Thr Asn Arg Gly Pro Ile Lys Phe Asn Val Trp
50                  55                  60

Asp Thr Ala Gly Gln Glu Lys Phe Gly Gly Leu Arg Asp Gly Tyr Tyr
65                  70                  75                  80

Ile Gln Ala Gln Cys Ala Ile Ile Met Phe Asp Val Thr Ser Arg Val
                85                  90                  95

Thr Tyr Lys Asn Val Pro Asn Trp His Arg Asp Leu Val Arg Val Cys
            100                 105                 110

Glu Asn Ile Pro Ile Val Leu Cys Gly Asn Lys Val Asp Ile Lys Asp
        115                 120                 125

Arg Lys Val Lys Ala Lys Ser Ile Val Phe His Arg Lys Lys Asn Leu
130                 135                 140

Gln Tyr Tyr Asp Ile Ser Ala Lys Ser Asn Tyr Asn Phe Glu Lys Pro
145                 150                 155                 160

Phe Leu Trp Leu Ala Arg Lys Leu Ile Gly Asp Pro Asn Leu Glu Phe
                165                 170                 175

Val Ala Met Pro Ala Leu Ala Pro Pro Glu Val Val Met Asp Pro Ala
            180                 185                 190

Leu Ala Ala Gln Tyr Glu His Asp Leu Glu Val Ala Gln Thr Thr Ala
        195                 200                 205

Leu Pro Asp Glu Asp Asp Leu
    210                 215

<210> SEQ ID NO 6
<211> LENGTH: 514
<212> TYPE: PRT
<213> ORGANISM: Homo sapiens

<400> SEQUENCE: 6

Met Ala Asp Tyr Leu Ile Ser Gly Gly Thr Gly Tyr Val Pro Glu Asp
1               5                   10                  15

Gly Leu Thr Ala Gln Gln Leu Phe Ala Ser Ala Asp Asp Leu Thr Tyr
            20                  25                  30

Asn Asp Phe Leu Ile Leu Pro Gly Phe Ile Asp Phe Ile Ala Asp Glu
        35                  40                  45

Val Asp Leu Thr Ser Ala Leu Thr Arg Lys Ile Thr Leu Lys Thr Pro
50                  55                  60

```
Leu Ile Ser Ser Pro Met Asp Thr Val Thr Glu Ala Asp Met Ala Ile
 65                  70                  75                  80

Ala Met Ala Leu Met Gly Gly Ile Gly Phe Ile His His Asn Cys Thr
                 85                  90                  95

Pro Glu Phe Gln Ala Asn Glu Val Arg Lys Val Lys Asn Phe Glu Gln
            100                 105                 110

Gly Phe Ile Thr Asp Pro Val Val Leu Ser Pro Ser His Thr Val Gly
            115                 120                 125

Asp Val Leu Glu Ala Lys Met Arg His Gly Phe Ser Gly Ile Pro Ile
            130                 135                 140

Thr Glu Thr Gly Thr Met Gly Ser Lys Leu Val Gly Ile Val Thr Ser
145                 150                 155                 160

Arg Asp Ile Asp Phe Leu Ala Glu Lys Asp His Thr Thr Leu Leu Ser
                165                 170                 175

Glu Val Met Thr Pro Arg Ile Glu Leu Val Val Ala Pro Ala Gly Val
                180                 185                 190

Thr Leu Lys Glu Ala Asn Glu Ile Leu Gln Arg Ser Lys Lys Gly Lys
            195                 200                 205

Leu Pro Ile Val Asn Asp Cys Asp Glu Leu Val Ala Ile Ile Ala Arg
210                 215                 220

Thr Asp Leu Lys Lys Asn Arg Asp Tyr Pro Leu Ala Ser Lys Asp Ser
225                 230                 235                 240

Gln Lys Gln Leu Leu Cys Gly Ala Ala Val Gly Thr Arg Glu Asp Asp
                245                 250                 255

Lys Tyr Arg Leu Asp Leu Leu Thr Gln Ala Gly Val Asp Val Ile Val
                260                 265                 270

Phe His Ser Ser Gln Gly Asn Ser Val Tyr Gln Ile Ala Met Val His
                275                 280                 285

Tyr Ile Lys Gln Lys Tyr Pro His Leu Gln Val Ile Gly Gly Asn Val
            290                 295                 300

Val Thr Ala Ala Gln Ala Lys Asn Leu Ile Asp Ala Gly Val Asp Gly
305                 310                 315                 320

Leu Arg Val Gly Met Gly Cys Gly Ser Ile Cys Ile Thr Gln Glu Val
                325                 330                 335

Met Ala Cys Gly Arg Pro Gln Gly Thr Ala Val Tyr Lys Val Ala Glu
                340                 345                 350

Tyr Ala Arg Arg Phe Gly Val Pro Ile Ile Ala Asp Gly Gly Ile Gln
                355                 360                 365

Thr Val Gly His Val Val Lys Ala Leu Ala Leu Gly Ala Ser Thr Val
                370                 375                 380

Met Met Gly Ser Leu Leu Ala Ala Thr Thr Glu Ala Pro Gly Glu Tyr
385                 390                 395                 400

Phe Phe Ser Asp Gly Val Arg Leu Lys Lys Tyr Arg Gly Met Gly Ser
                405                 410                 415

Leu Asp Pro Met Glu Lys Ser Ser Ser Gln Lys Arg Tyr Phe Ser
            420                 425                 430

Glu Gly Asp Lys Val Lys Ile Ala Gln Gly Val Ser Gly Ser Ile Gln
            435                 440                 445

Asp Lys Gly Ser Ile Gln Lys Phe Val Pro Tyr Leu Ile Ala Gly Ile
            450                 455                 460

Gln His Gly Cys Gln Asp Ile Gly Ala Arg Ser Leu Ser Val Leu Arg
465                 470                 475                 480
```

Ser Met Met Tyr Ser Gly Glu Leu Lys Phe Glu Lys Arg Thr Met Ser
            485                 490                 495

Pro Gln Ile Glu Gly Gly Val His Gly Leu His Ser Tyr Glu Lys Arg
        500                 505                 510

Leu Tyr

<210> SEQ ID NO 7
<211> LENGTH: 254
<212> TYPE: PRT
<213> ORGANISM: Homo sapiens

<400> SEQUENCE: 7

Met Ala Ala Tyr Lys Leu Val Leu Ile Arg His Gly Glu Ser Ala Trp
1               5                   10                  15

Asn Leu Glu Asn Arg Phe Ser Gly Trp Tyr Asp Ala Asp Leu Ser Pro
            20                  25                  30

Ala Gly His Glu Glu Ala Lys Arg Gly Gly Gln Ala Leu Arg Asp Ala
        35                  40                  45

Gly Tyr Glu Phe Asp Ile Cys Phe Thr Ser Val Gln Lys Arg Ala Ile
    50                  55                  60

Arg Thr Leu Trp Thr Val Leu Asp Ala Ile Asp Gln Met Trp Leu Pro
65                  70                  75                  80

Val Val Arg Thr Trp Arg Leu Asn Glu Arg His Tyr Gly Gly Leu Thr
                85                  90                  95

Gly Leu Asn Lys Ala Glu Thr Ala Ala Lys His Gly Glu Ala Gln Val
            100                 105                 110

Lys Ile Trp Arg Arg Ser Tyr Asp Val Pro Pro Pro Met Glu Pro
        115                 120                 125

Asp His Pro Phe Tyr Ser Asn Ile Ser Lys Asp Arg Arg Tyr Ala Asp
    130                 135                 140

Leu Thr Glu Asp Gln Leu Pro Ser Cys Glu Ser Leu Lys Asp Thr Ile
145                 150                 155                 160

Ala Arg Ala Leu Pro Phe Trp Asn Glu Glu Ile Val Pro Gln Ile Lys
                165                 170                 175

Glu Gly Lys Arg Val Leu Ile Ala Ala His Gly Asn Ser Leu Arg Gly
            180                 185                 190

Ile Val Lys His Leu Glu Gly Leu Ser Glu Glu Ala Ile Met Glu Leu
        195                 200                 205

Asn Leu Pro Thr Gly Ile Pro Ile Val Tyr Glu Leu Asp Lys Asn Leu
    210                 215                 220

Lys Pro Ile Lys Pro Met Gln Phe Leu Gly Asp Glu Glu Thr Val Arg
225                 230                 235                 240

Lys Ala Met Glu Ala Val Ala Ala Gln Gly Lys Ala Lys Lys
                245                 250